United States Patent
Inoue et al.

(10) Patent No.: US 7,387,611 B2
(45) Date of Patent: Jun. 17, 2008

(54) PHYSICAL MOVEMENT ANALYZER AND PHYSICAL MOVEMENT ANALYZING METHOD

(75) Inventors: Shigeyuki Inoue, Kyotanabe (JP); Shinji Tanaka, Ibaraki (JP); Takako Shiraishi, Ikoma (JP); Hiroshi Yamamoto, Shijonawate (JP); Yoshitaka Kawasaki, Nabari (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 717 days.

(21) Appl. No.: 10/817,880

(22) Filed: Apr. 6, 2004

(65) Prior Publication Data

US 2004/0230138 A1    Nov. 18, 2004

(30) Foreign Application Priority Data

| Apr. 10, 2003 | (JP) | ............................. 2003-106680 |
| Apr. 14, 2003 | (JP) | ............................. 2003-109288 |
| May 9, 2003 | (JP) | ............................. 2003-132392 |

(51) Int. Cl.
  *A61B 5/103*    (2006.01)
  *A61B 5/117*    (2006.01)
  *G01B 5/02*    (2006.01)

(52) U.S. Cl. ..................... 600/595; 600/585; 702/160; 73/488

(58) Field of Classification Search ............... 702/160; 600/595, 587; 73/488
See application file for complete search history.

(56) References Cited

U.S. PATENT DOCUMENTS 6,301,964 B1    10/2001 Fyfe et al.

2002/0002863 A1 *   1/2002 Slycke et al. .................. 73/488

FOREIGN PATENT DOCUMENTS

| JP | 5-180861 | 7/1993 |
| JP | 5-274434 | 10/1993 |
| JP | 2760472 | 3/1998 |

(Continued)

OTHER PUBLICATIONS

Zijlstra, W., et al. "Displacement of the pelvis during human walking: experimental data and model predictions" Dec. 1997 Gait and Posture 6 (249-262).*

(Continued)

*Primary Examiner*—Max Hindenburg
*Assistant Examiner*—Emily M Lloyd
(74) *Attorney, Agent, or Firm*—Wenderoth, Lind & Ponack, L.L.P.

(57) ABSTRACT

An acceleration information detecting unit of an acceleration detecting apparatus having an acceleration sensor with at least one axis that measures acceleration in a back and forth direction (or a right and left direction) of a walking person. Acceleration data indicating the acceleration is sent to a wireless communication control unit. The wireless communication control unit sends the acceleration data to a physical movement analyzer using a short-distance wireless communication method. On the other hand, the wireless communication control unit of the physical movement analyzer receives the acceleration data that is sent from the acceleration detecting apparatus using a short-distance wireless communication method and sends it to a walking speed detecting unit. The walking speed detecting unit estimates strides and walking period based on the received acceleration data and calculates the walking speed based on the strides and the walking period.

14 Claims, 23 Drawing Sheets

FOREIGN PATENT DOCUMENTS

| | | |
|---|---|---|
| JP | 10-111940 | 4/1998 |
| JP | 10-165395 | 6/1998 |
| JP | 2003-006608 | 1/2003 |

OTHER PUBLICATIONS

Sekine, M., et al., entitled "*Assessment of Gait Parameter in Hemiplegic Patients by Accelerometry*", Proceedings of the 22nd Annual International Conference of the IEEE Engineering in Medicine and Biology Society, vol. 3, Jul. 23, 2000, pp. 1879-1882, XP010530872.

Waarsing, J.H., et al., entitled "*Quantifying the Stability of Walking Using Accelerometers*", Engineering in Medicine and Biology Society, 1996. Bridging Disciplines for Biomedicine., 18th Annual International Conference of the IEEE Amsterdam, Netherlands Oct. 31-Nov. 3, 1996, New York, NY, USA, IEEE, US, Oct. 31, 1996, pp. 469-4470, XP010262084.

Sabatini, A.M., et al., entitled "*Portable System for Data Acquisition and Transmission Based on Handheld PC Technology*", Electronics Letters, IEE Stevenage, GB, vol. 38, No. 25, Dec. 5, 2002, pp. 1635-1637, XP006019430.

Miyazaki, S., entitled "*Long-Term Unrestrained Measurement of Stride Length and Walking Velocity Utilizing a Piezoelectric Gyroscope*", IEEE Transactions on Biomedical Engineering, IEEE Inc. New York, US, vol. 44, No. 8, Aug. 1, 1997, pp. 753-759, XP000701741.

Auvinet, B., et al., entitled "*Accelerometric Gait Analysis for Use in Hospital Outpatients*", Revue Du Rhumatisme, Expansion Scientifique Francaise, Paris, FR, vol. 66, No. 7/9, 1999, pp. 389-397, XP000922614.

\* cited by examiner (Back and forth direction)

(Right and left direction)

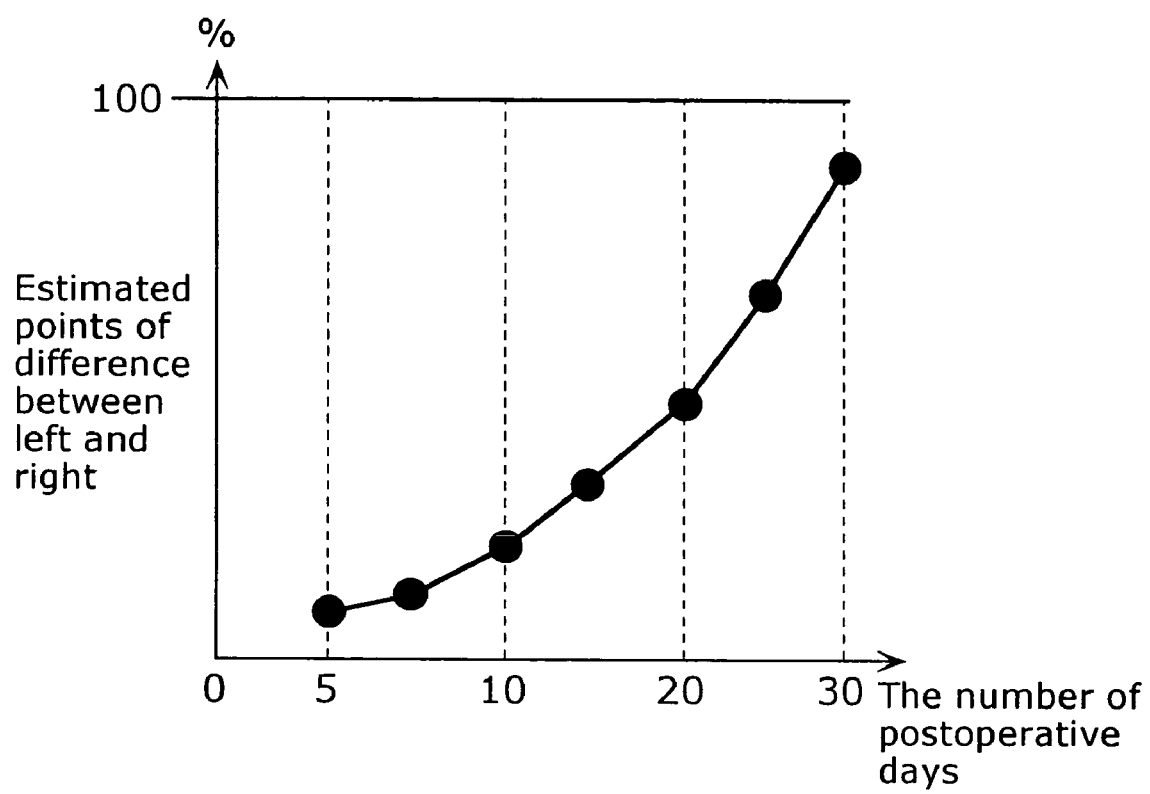

PHYSICAL MOVEMENT ANALYZER AND PHYSICAL MOVEMENT ANALYZING METHOD

BACKGROUND OF THE INVENTION (1) Field of the Invention

The present invention relates to a physical movement analyzer for performing analysis on postures and movements based on physical feature amounts that are extracted at the time when a human moves. More specifically, the present invention relates to a physical movement analyzer or the like that is used for a walking ability test in a rehabilitation system or a sport training system.

(2) Description of the Related Art

In view of the status of a recently aging society, apparatuses and medical treatments for rehabilitating elderly people or people with a leg disorder have drawn attention. Especially, quantitatively grasping the degree of recovery from a leg disorder (or deterioration of a leg disorder) of a patient with an artificial joint, a patient with a degenerative joint disease or the like is an important problem, and thus apparatuses or the like for solving this problem have been proposed conventionally. For example, refer to Japanese Laid-Open Patent application No. 1998-111940 (related art 1), Japanese Laid-Open Patent application No. 1993-180861 (related art 2) and Japanese Laid-Open Patent application No. 1993-274434 (related art 3).

The "body feature point detecting apparatus and physical movement analyzer" of the related art 1 performs movement analysis based on collected characteristics of physical movements for every human body part by shooting physical movements. Also, the "movement analyzer" of the related art 2 includes magnetic sensors corresponding to respective human body parts that detect the magnetic parts that are formed on a magnetic recording medium so as to measure movement amount quantitatively. Further, in addition, in the "movement analyzing method and its apparatus" of the related art 3, a bright gage mark is attached to a part of a human body so that the moving object can be recorded and a movement analysis is performed based on the trajectory of the gage mark.

Also, in general, deteriorated posture retention of the elderly people is the fundamental cause that makes them topple over to be a bedbound person. This deteriorated posture retention is remarkably observable in walking. In the case of elderly people, for example, deterioration in posture retention reduces walking speed and narrows walking strides. As a compensation for this, they enlarge the distance between the right leg and the left leg (called "stance" from here) so as to secure stability.

Therefore, there is a need to measure stances at the time of walking. In general, Gravicorders are used as a tool for performing human movement analysis. The feature of this technique is to perform movement analysis of the center of gravity at the time when a person gets on the load detection board which is previously set on a straight floor. For example, refer to Patent No. 2760472, related art 4.

However, in a technique using an image analyzing method and the like shown in the above-mentioned related art 1 to 3, it takes a lot of labor to collect and analyze data because the handling of the data is huge and redundant, and thus there emerges a problem that it is rarely used at sites of rehabilitation or sports training which have restrictions on time, cost and so on.

Also, in the case of the technique shown in the above-mentioned related art 4, areas where a person makes movements, kinds of movements, postures and the like are limited because measurement of human physical movements (trajectory) should be done by making a person get on the load detection board, which is troublesome for a person and a measurer (for example, a medical staff member and a caregiver). Also, in this case, there is a problem that measuring a walking state is impossible.

SUMMARY OF THE INVENTION

The present invention is conceived in view of the above-mentioned problems. An object of the present invention is to provide a movement analyzer and the like for quantitatively analyzing human posture and movement in a time saving and cost saving manner.

In order to achieve the above-mentioned object, the physical movement analyzer for analyzing a human walking ability concerning the present invention includes an acceleration detecting unit operable to detect an acceleration of a person moving in a certain direction, an acceleration analyzing unit operable to extract a specified physical feature amount by performing a predetermined analysis on the detected acceleration, and a walking ability value calculating unit operable to calculate a physical quantity concerning the human walking ability based on the extracted physical feature amount.

In this way, acceleration data that is received from an acceleration sensor satisfies the requirement for calculating the movements of a person, which does not make a person and a measurer feel troublesome at the time of measurement and makes it possible to analyze walking of a person in a time and cost saving manner.

Also, in order to achieve the above-mentioned object, the physical movement analyzing system includes an acceleration detecting apparatus and includes an analyzer for analyzing a human's walking ability. The acceleration detecting apparatus includes an acceleration detecting unit operable to detect an acceleration of a person moving in a certain direction, and an acceleration sending unit operable to transform the detected acceleration into an electric signal and send an electric signal to the analyzer. The analyzer includes an acceleration receiving unit operable to receive the electric signal from the acceleration detecting apparatus and transform the electric signal into the detected acceleration, includes an acceleration analyzing unit operable to extract a specified physical feature amount by performing a predetermined analysis on the transformed detected acceleration, and includes a walking ability value calculating unit operable to calculate the physical quantity concerning a human's walking ability based on the extracted physical feature amount.

In this way, measuring acceleration using acceleration sensors that are attached to a person satisfies the requirement for calculating the movements of a person, which does not make a person and a measurer feel troublesome at the time of measurement and makes it possible to provide a physical movement analyzing system capable of analyzing the walking ability of a person in a time and cost saving manner.

Also, in order to achieve the above-mentioned object, the present invention can be realized as a physical analyzing method comprising steps that correspond to the respective characteristic units of the above-mentioned physical movement analyzer or as a program comprising all the steps. The program can be distributed via a recording medium such as a CD-ROM or a transmission medium such as a communication network as well as can be stored in a ROM or the like that is installed in a physical movement analyzer.

With the physical movement analyzing system concerning the present invention, acceleration in the back and forth direction and acceleration in the right and left direction at the time of walking are measured by acceleration sensors with at least one axis, and strides, walking speed and the like are quantitatively calculated based on these accelerations, which makes it possible to quantitatively indicate the recovery level of the physical ability of a patient with an artificial joint, a patient with a degenerative joint disease or the like in a time and cost saving manner. This invention is expected to be utilized at sites of rehabilitation or sports training which have a restriction on time for medical treatments, labor, cost and so on.

Also, having a person watch the status of physical ability such as his/her walking makes it possible to share the problem concerning the recovery condition between medical staff members and a patient, and thus it becomes possible to help patients with their rehabilitation effectively.

Further, the physical movement analyzing system concerning the present invention entails few limits at the time of measurement and makes it possible to analyze walking stances in a time and cost saving manner.

Furthermore, the physical movement analyzing system concerning the present invention entails few limits at the time of measurement and makes it possible to detect the difference between a right leg and a left leg at the time of physical movements in a time and cost saving manner quantify the degree of functional recovery or deterioration with ease.

FURTHER INFORMATION ABOUT TECHNICAL BACKGROUND TO THIS APPLICATION

Japanese Patent application No. 2003-106680 filed on Apr. 10, 2003, is incorporated herein by reference, Japanese Patent application No. 2003-109288 filed on Apr. 14, 2003, is incorporated herein by reference, and Japanese Patent application No. 2003-132392 filed on May 9, 2003 is incorporated herein by reference.

BRIEF DESCRIPTION OF THE DRAWINGS

These and other advantages and features of the invention will become apparent from the following description thereof taken in conjunction with the accompanying drawings that illustrate a specific embodiment of the invention. In the Drawings:

FIG. 24 is a diagram showing how the person's estimated points of difference between left and right is displayed on the terminal of a remote place.

DETAILED DESCRIPTION OF THE INVENTION

Embodiments concerning the present invention will be explained in detail with reference to figures. The present invention will be explained with reference to figures in the following embodiments, but the present invention is not limited to this.

First Embodiment

Figure 1:
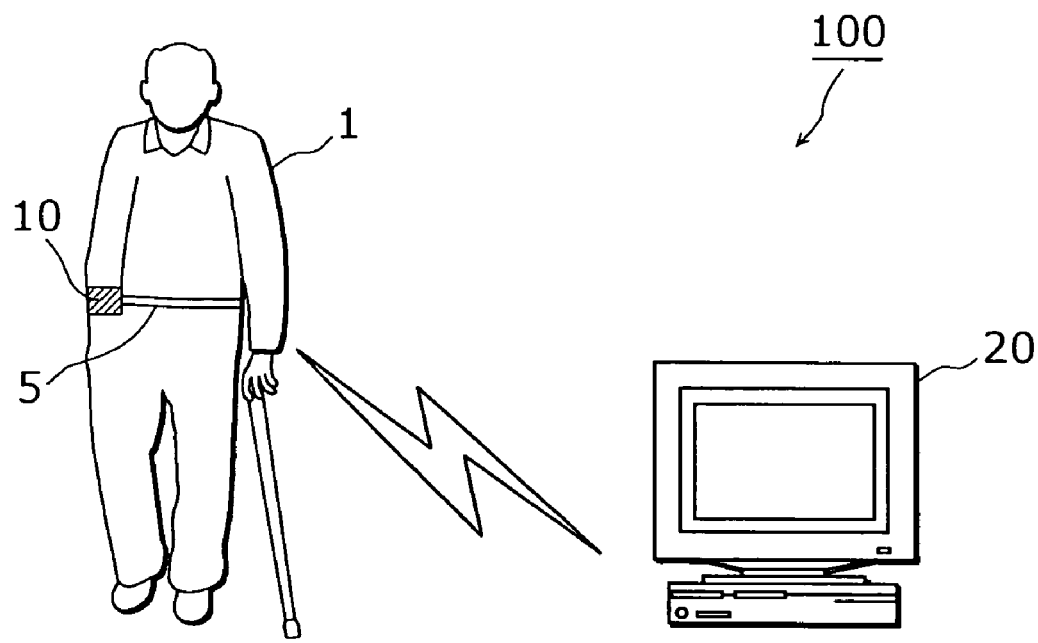
FIG. 1 is an outline diagram of a physical movement analyzing system in the first embodiment.

FIG. 1 is an outline diagram of a physical movement analyzing system 100 in this embodiment. This physical movement analyzing system 100 is a system for calculating strides or walking speed based on the acceleration data that is obtained from the person 1 who is walking and comprises an acceleration detecting apparatus 10 and a physical movement analyzer 20.

The acceleration detecting apparatus 10 is for making an internal acceleration sensor measure the acceleration of the walking person 1 and sending the data to the physical movement analyzer 20 by air (for example, a communication method based on Bluetooth, that is, a trademark of "the Bluetooth SIG incorporated"), and the acceleration detecting apparatus 10 is fixed at a body part of the person 1 (for example, a patient with a leg malfunction). The following explanation is on an embodiment where the acceleration in the back and forth direction or in the left and right direction of the walking person 1 is measured and walking speed based on the measured acceleration is calculated in the case where the acceleration detecting apparatus 10 is attached to the right waist of the person 1.

The physical movement analyzer 20 has functions of general personal computers and also a function for receiving the acceleration data that is sent from the acceleration detecting apparatus 10 using a communication method based on the above-mentioned Bluetooth and calculating strides and walking speed of a person based on this acceleration data.

Figure 2:
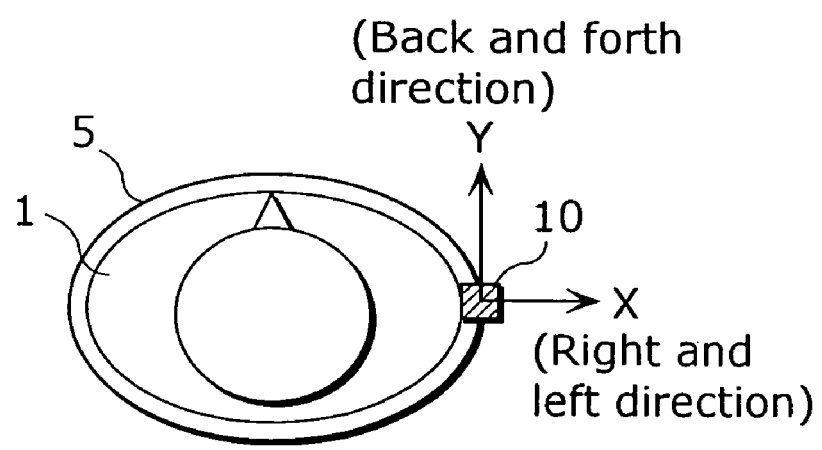
FIG. 2 is a diagram showing the relation between the set location of the acceleration detecting apparatus and the coordinate axes of an acceleration sensor in the present invention.

FIG. 2 is a diagram showing the relation between the install location of the acceleration detecting apparatus and the coordinate axis of the acceleration sensor in the present invention. The relation between the install location of the acceleration detecting apparatus and the coordinate axis of the acceleration sensor explained below is not limited to this embodiment, and it is common in the following embodiments 2 to 4. As shown in FIG. 2, the acceleration detecting apparatus 10 is fixed at the right waist of the person 1 by using, for example, a belt-shape placing tool 5. Also, in the present invention, at the time of measuring the acceleration while the person 1 is walking, the left and right direction is determined as the X-axis (the right direction is determined as "positive direction") and the back and forth direction is determined as the Y-axis (the forth direction is determined as "positive direction").

Figure 3:
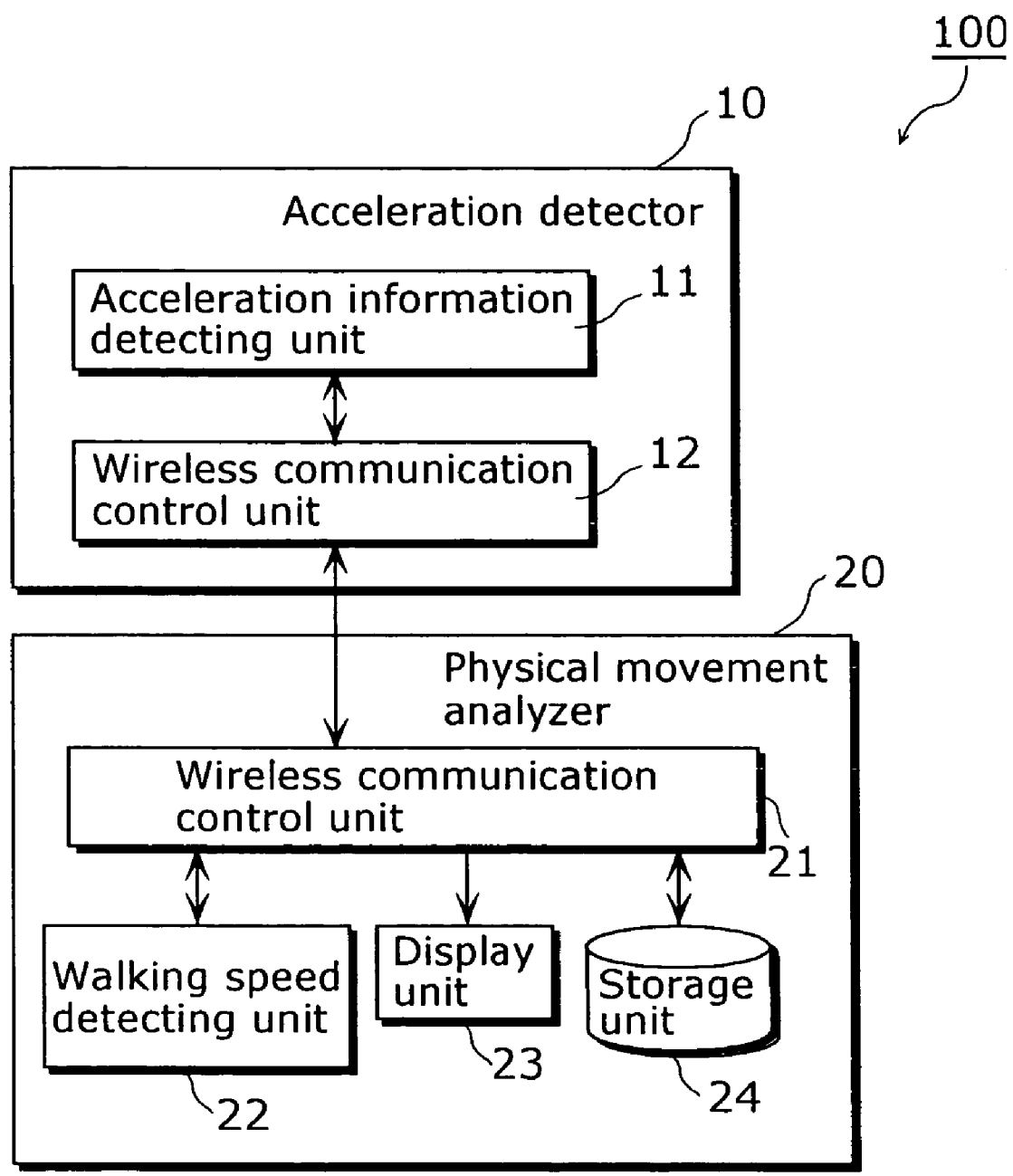
FIG. 3 is a block diagram showing the functional structure of the acceleration detecting apparatus and the functional structure of the physical movement analyzer in the first embodiment.

FIG. 3 is a block diagram showing the functional structure of the above-mentioned acceleration detecting apparatus 10 and the functional structure of the physical movement analyzer 20. As shown in FIG. 3, the acceleration detecting apparatus 10 comprises an acceleration information detecting unit 11 and a wireless communication control unit 12. On the other hand, the physical movement analyzer 20 comprises a wireless communication control unit 21, a walking speed detecting unit 22, a display unit 23 and a storage unit 24. Also, the acceleration detecting apparatus 10 will be explained.

The acceleration information detecting unit 11 includes, for example, an IC-type acceleration sensor (for example, the one capable of measuring two-axes acceleration) for measuring the acceleration in the back and forth direction (or left and right direction) of the moving person 1, and sends the information indicating this acceleration ("acceleration data") to the wireless communication control unit 12. To be more specific, for example, the acceleration information detecting unit 11 performs monitoring of the acceleration in the back and forth direction while the person 1 is walking for a predetermined period of time (for example, for 10 seconds), performs sampling voltage changes that occurred according to the acceleration of maximum±2G (1G=9.8 [m/s$^2$]) using a sampling frequency of 125 Hz and quantization bits of 16 bits so as to perform A/D conversion, and sends the converted acceleration on which A/D conversion is performed data to the wireless communication control unit 12.

The wireless communication control unit 12 is a CPU including, for example, a ROM or a RAM for storing a control program or the like and controls the whole acceleration detecting apparatus 10. Further, the wireless communication control unit 12 sends the acceleration data measured in the acceleration information detecting unit 11 to the physical movement analyzer 20 by using a communication method such as the above-mentioned Bluetooth.

Next, the physical movement analyzer 20 will be explained.

The wireless communication control unit 21 is a CPU including a ROM or a RAM for storing a control program or the like the wireless communication control unit 12 in the above-mentioned acceleration detecting apparatus 10 and controls the whole physical movement analyzer 20. Further, the wireless communication control unit 21 receives the acceleration data sent from the acceleration detecting apparatus 10 by using, for example, a communication method based on the above-mentioned Bluetooth and sends it to the walking speed detecting unit 22.

The walking speed detecting unit 22 calculates the strides and the walking period based on the received acceleration data and walking speed based on the strides and the walking period.

The display unit 23 is a display apparatus with, for example, a liquid crystal panel and displays information concerning the person's 1 posture or movements (for example, measurement values of the walking speed, the way the person recovered from his/or functional disorder, etc.) or information for advice or the like in response to the wireless communication control unit 21.

The storage unit 24 is, for example, a recording apparatus comprising a RAM, a fixed disc or the like, records information indicating the acceleration that is received from the acceleration detecting apparatus 10 and information indicating the walking speed that is calculated by the walking speed detecting unit 22 ("walking speed data").

Here, the method for calculating the walking speed based on the acceleration data will be explained in detail with reference to FIGS. 4 to 6.

Figure 4:
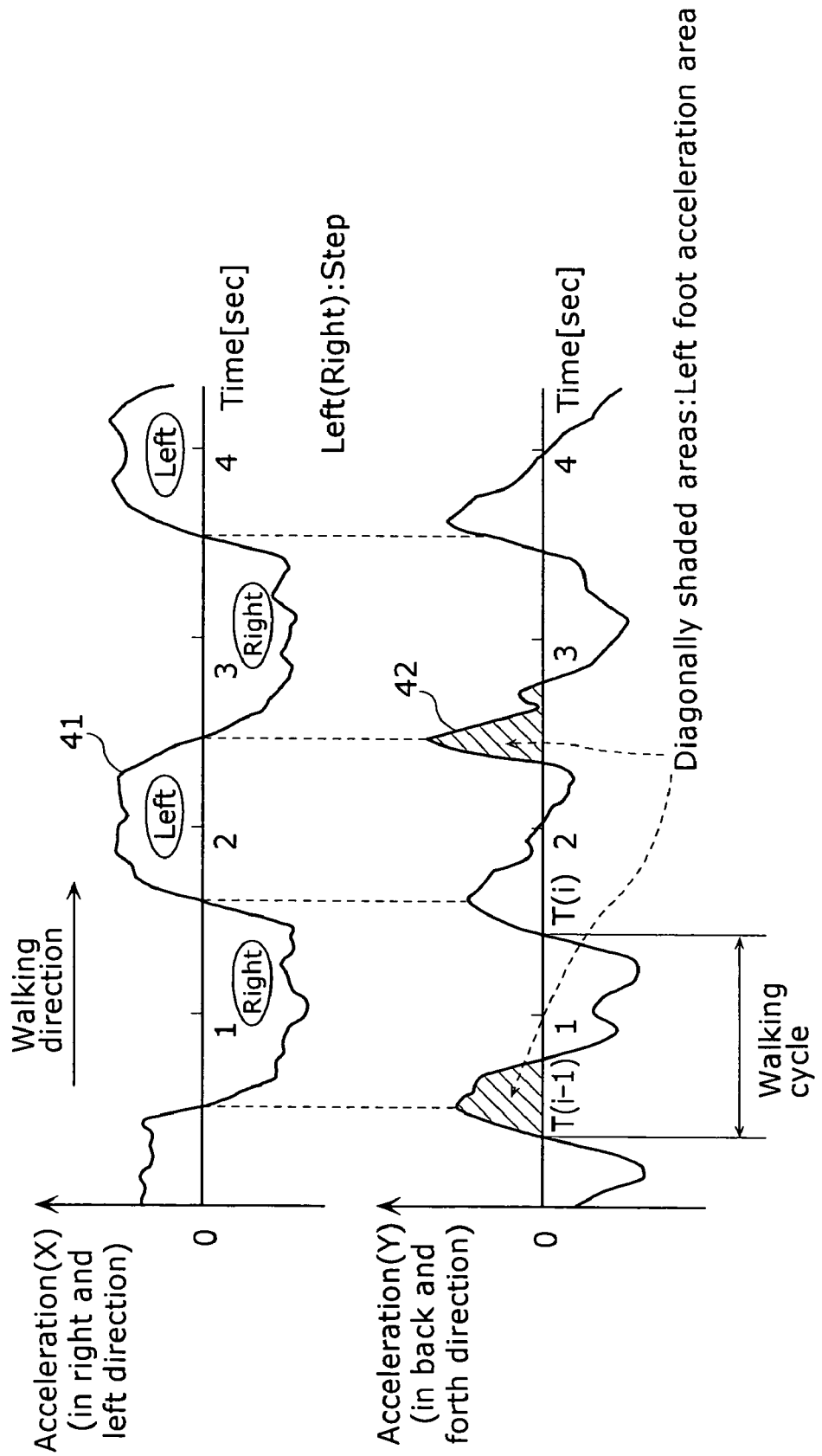
FIG. 4 is an example showing the correlation between the steps and the change in acceleration in a walking ability test performed on a person in a certain duration.

FIG. 4 is an example indicating the relation between the steps and the change in acceleration in the walking ability test performed on the person for a certain duration. The curve 41 in FIG. 4 is a diagram indicating the change in acceleration in the right and left direction at the time when the person 1 received the walking ability test. On the other hand, the curve 42 is a diagram indicating the change in acceleration in the back and forth direction at the time the above-mentioned walking ability test is performed. As explained in the above-mentioned FIG. 2, in the case of the acceleration in the right and left direction, "rightward" is determined as the positive direction, and in the case of the acceleration in the back and forth direction, "forward" is determined as the positive direction. In this embodiment, the definition of the walking speed in the following formula (1) will be used in this embodiment.

$$\text{Walking speed} = (\text{walking period}) \times (\text{strides}) \tag{1}$$

Here, the "walking period" in the above-mentioned formula (1), is the average (for example, the average of 10 cycles that corresponds to "T(i)−T(i−1)[sec]" period of the curve 42 in FIG. 4 (in other words, the change in acceleration in the back and forth direction). In this case, in the above-mentioned curve 42, adjacent two points that cross at "0" in the process of changing from a negative value to a positive value are used.

Further, as to "strides" in the above-mentioned formula (1), for example, Fourier transform is performed on the curve 42 of the acceleration in the back and forth direction that is measured according to the above-mentioned 10 cycles so as to calculate a power spectrum and further, the common logarithm of the peak value (this is called "frequency power").

Figure 5:
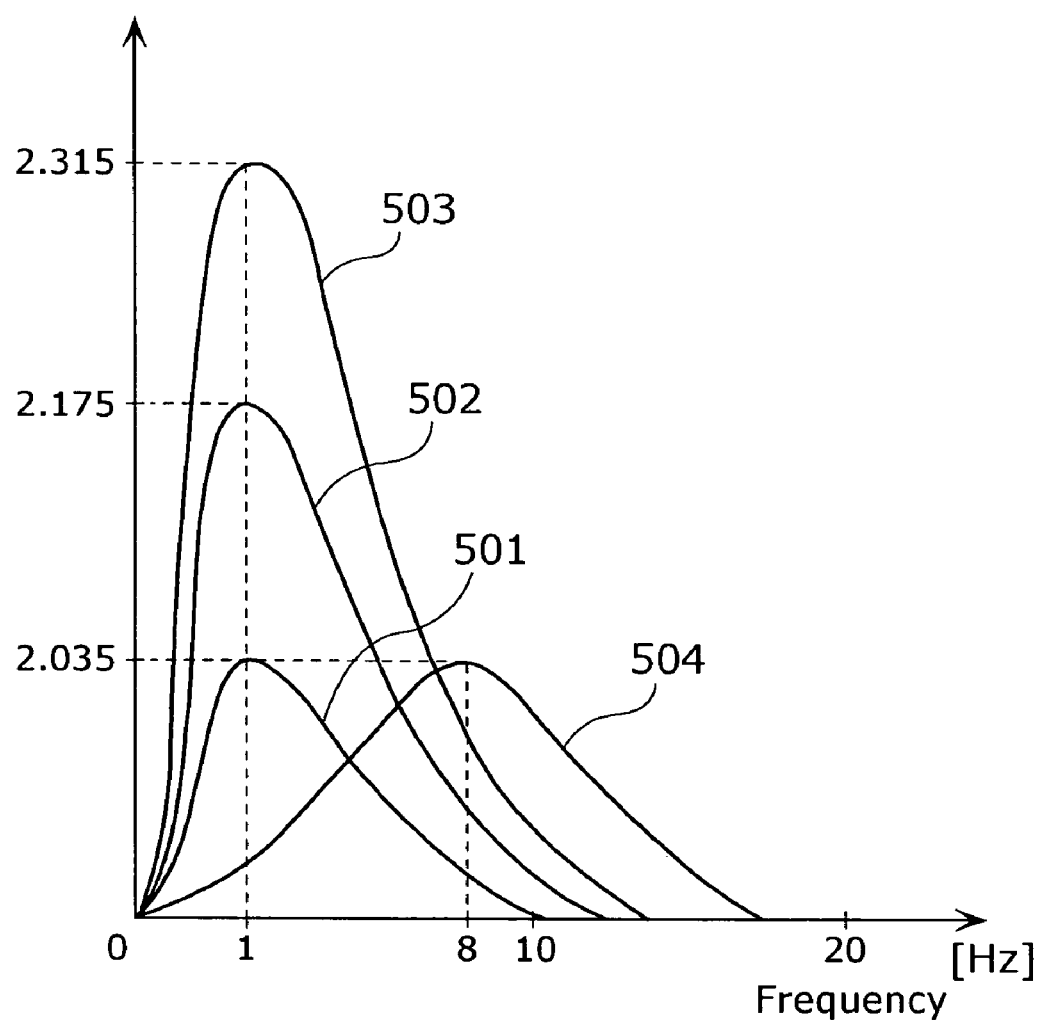
FIG. 5 is a schematic diagram showing the frequency spectrum concerning the acceleration curve in the back and forth direction.

FIG. 5 is a schematic diagram showing the frequency spectrum concerning the above-mentioned curve 42. In the example shown in FIG. 5, the example where the frequency power becomes maximum (curve 501 to 504) at the time when the frequency is "1" (in other words, it takes one second for a step), the common logarithm of each maximum power is indicated. Therefore, in the case of the curve 504 in FIG. 5, the person walked eight steps per second.

Figure 6:
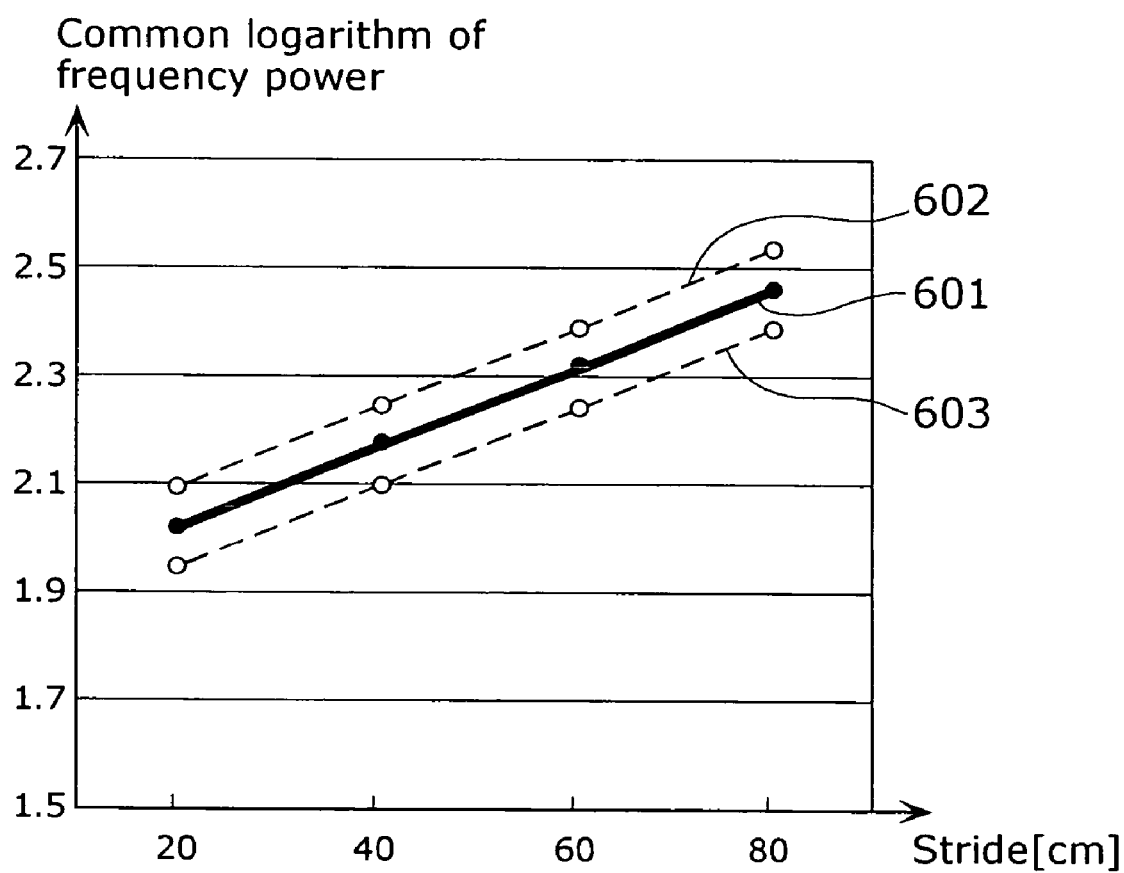
FIG. 6 is an example showing the relation between a common logarithm of frequency power and strides that are calculated empirically.

FIG. 6 is an example indicating the relation between the common logarithm of the frequency power that is calculated empirically and strides. As shown in FIG. 6, the common logarithm of the maximum frequency power and the strides are in proportionality. The following formula (2) is derived based on the curve 601 in FIG. 6 (here, the unit of strides is "cm")

$$\text{Strides}=143\times(\text{the common logarithm of the maximum frequency power})-271 \qquad (2)$$

As to the above-mentioned relation, a single curve may be defined for each person (therefore, in the case where there are three persons, three curves, for example, the curves 601 to 603 may be defined).

As is clear from the above-mentioned explanation, it becomes possible to calculate the "walking speed" by substituting the "stride" that is calculated in the above-mentioned formula (2) in the above-mentioned formula (1).

Next, the operation of the physical movement analyzer 20 that is formed as shown above will be explained.

Figure 7:
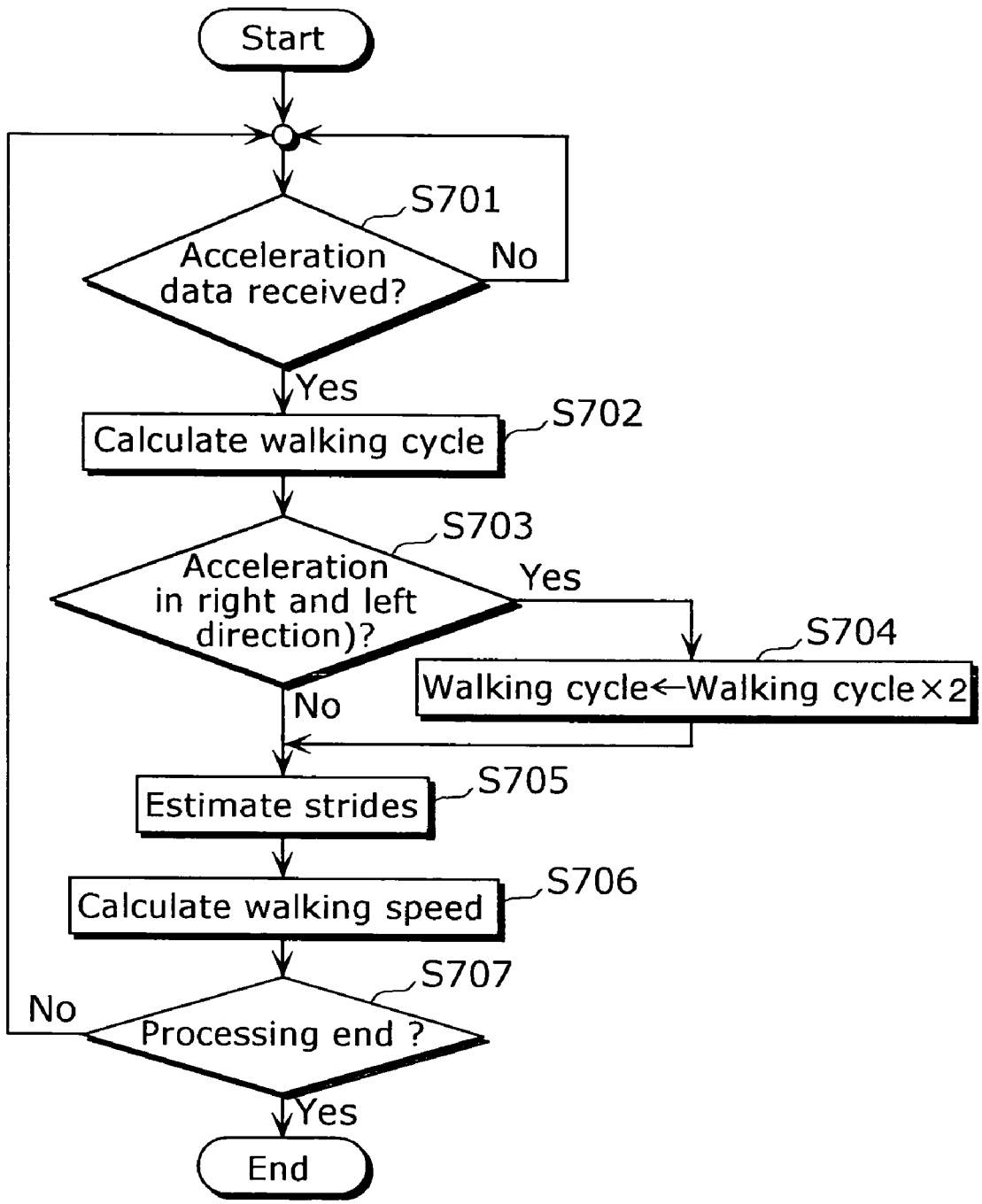
FIG. 7 is a flow chart showing the processing flow of the physical movement analyzer.

FIG. 7 is a flow chart showing the processing flow of the physical movement analyzer 20.

First, the wireless communication control unit 21 receives acceleration data that is sent from the acceleration detecting apparatus 10 (S701: Yes), and calculates the walking period based on this acceleration data (S702). Next, the wireless communication control unit 21 doubles the value of the calculated walking period (S704) in the case where the received acceleration data is in the right and left direction (S703: Yes). Further, the wireless communication control unit 21 estimates the stride (S705) based on the received acceleration data, and calculates the walking speed based on the above-mentioned walking period and the strides (S706). Next, if the processing is finished (S707: Yes), then the physical movement analyzer stops analyzing. However, if the processing is not finished (S707: No), then the wireless communication control unit 21 continues to check for received data (S701).

Here, the effective variation of the physical movement analyzing system 100 will be explained.

Figure 8:
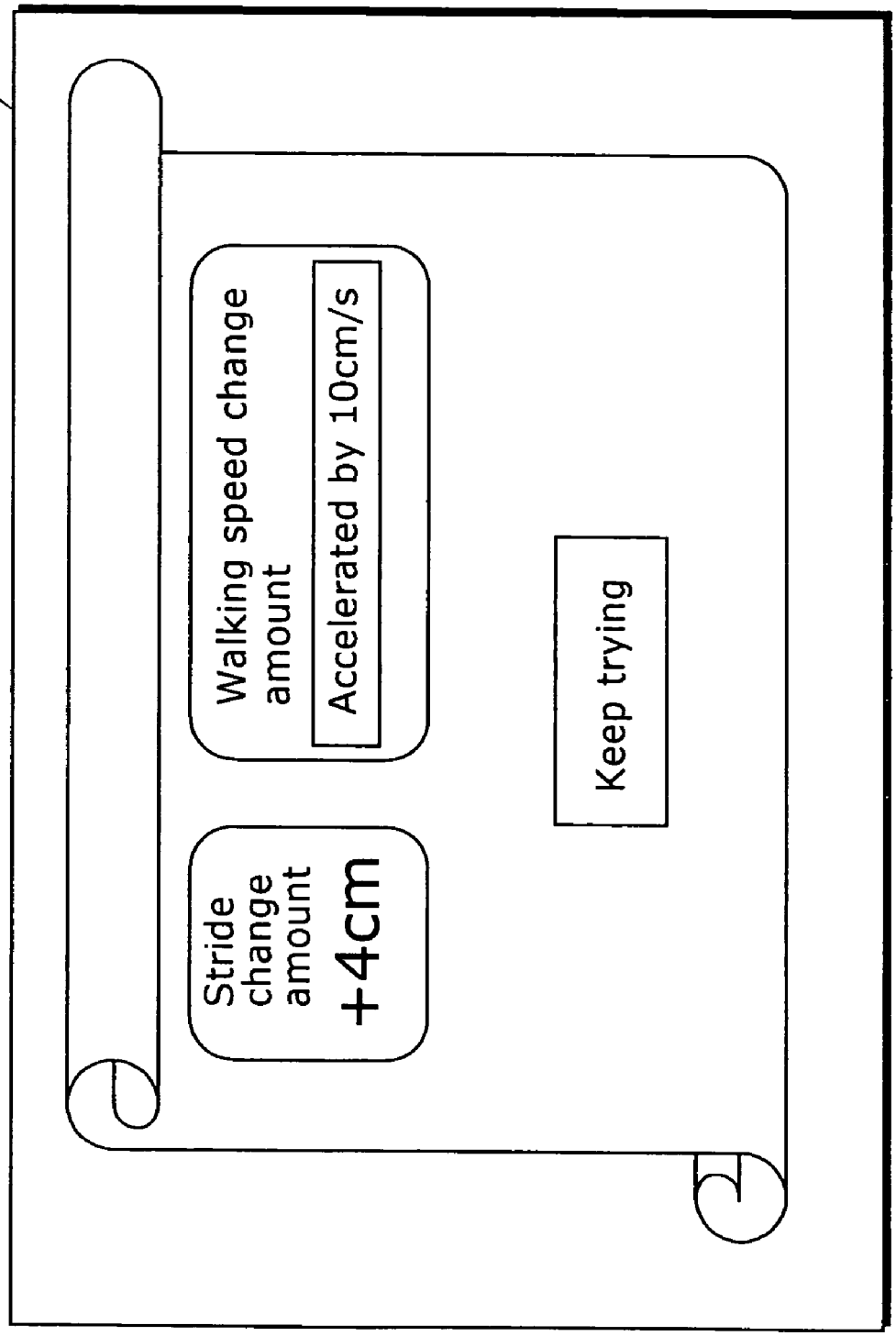
FIG. 8 is a display example in the case of comparing the latest measurement values of strides and walking speed with the previous values in the display unit.

FIG. 8 is an example 801 in the case where the latest measurement values of the strides and the walking speed are compared with the previous measurement values in the display unit 23.

Figure 9:
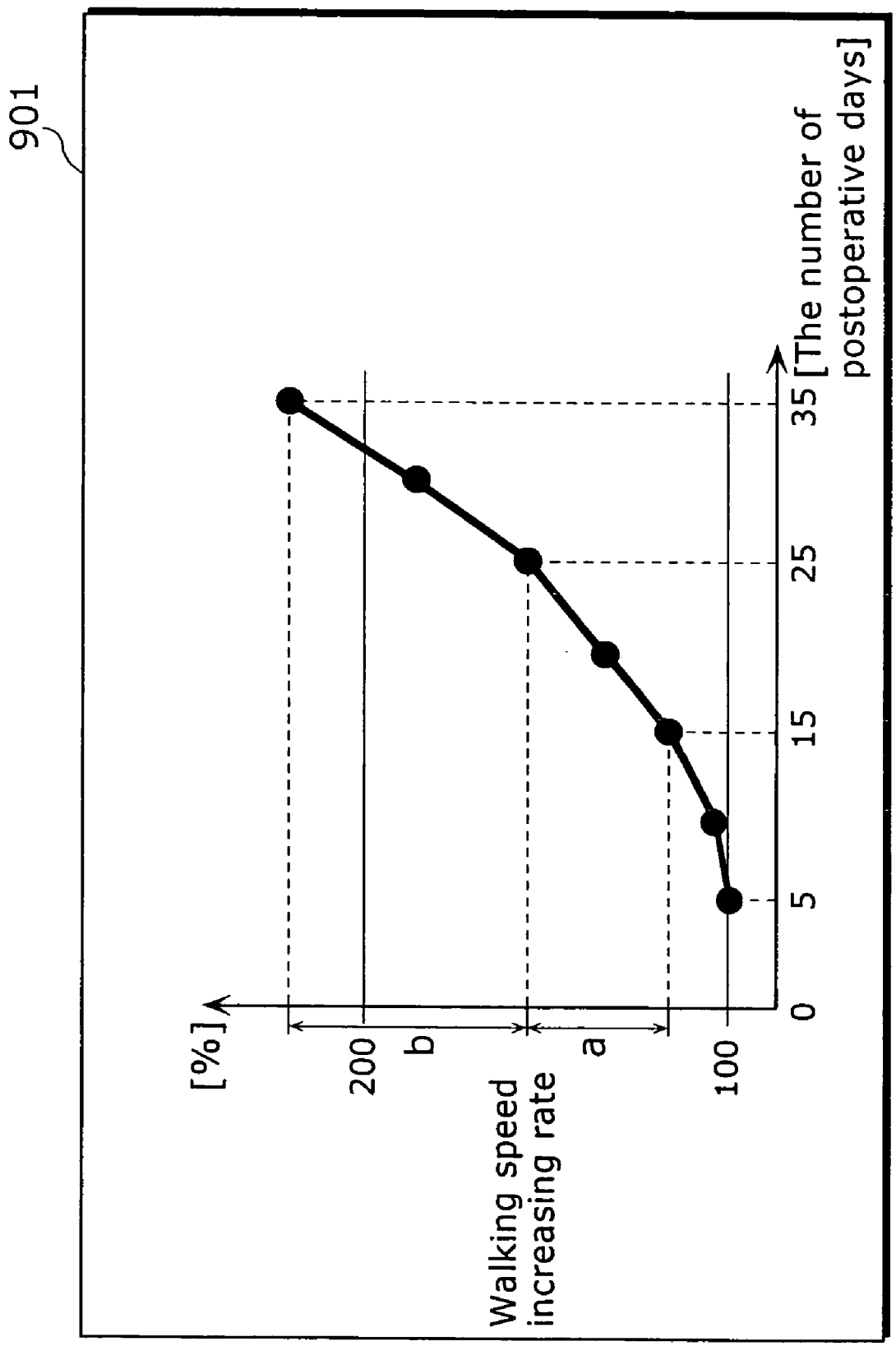
FIG. 9 is an example showing the change of a physical movement ability concerning a person.

Further, FIG. 9 is an example 901 indicating the change in the physical movement ability concerning the person 1, and a graph indicating how there appears to be a change in walking speed of a target patient who experienced a hip replacement operation in the rehabilitation process after the operation. The example of FIG. 9 is a diagram indicating the change rate of the walking speed after the operation in relation to the elapsed time in the case where the first measurement started from the fifth day after the operation and the first measurement value is considered to be 100. As is clear from the example in FIG. 9, the display unit 23 has a counting function for every 10 days.

As shown up to this point, using the physical movement analyzing system 100 concerning this embodiment makes it possible to calculate the strides, walking periods and walking speed based on the acceleration that is measured by the acceleration sensor with at least one axis (in the back and forth direction, in the right and left direction and the like) that is attached to the person, which makes it possible to realize the physical movement analysis in a time and cost saving manner in the rehabilitation system or the sports training system.

In the above-mentioned embodiment 1, "forward" is determined as the positive direction as to the acceleration in the back and forth direction, and "rightward" is determined as the positive direction as to the acceleration in the right and left direction, but embodiments are not limited to them, it is also possible to define positive/negative of each acceleration value based on other definition. Also, an embodiment for presenting information necessary for the display unit 23 has been shown in the above-mentioned embodiment, but embodiments are not limited to this, for example, information may be notified by sound, stimulus such as vibration, a flasher or the like.

Also, the above-mentioned embodiment is formed in a way that the acceleration in the back and forth direction is detected as shown in FIG. 4 and walking period, strides and walking speed are calculated based on the detected acceleration, but the walking period may be calculated based on the acceleration in the right and left direction and strides may be calculated based on the acceleration in the back and forth direction. Note that the walking period in this case is calculated based on the acceleration in the above-mentioned back and forth direction and the obtained walking period corresponds to the half of the walking period.

Also, the above-mentioned embodiment shows an embodiment for sending the acceleration data from the acceleration detecting apparatus 10 to the physical movement analyzer 20 using a short-distance wireless communication, but the embodiment may be formed so that a single apparatus can equip all the functions of the above-mentioned acceleration detecting apparatus 10 and the physical movement analyzer 20.

Further, the above-mentioned embodiment shows an example where the acceleration while the person is walking is measured, but embodiments are not limited to the acceleration by walking, it is also possible to have a person perform other cyclical movements and analyze person's physical movement abilities by measuring the acceleration.

Second Embodiment

The above-mentioned first embodiment explains a physical movement analyzing system for calculating the strides and the walking speed based on the acceleration data that is obtained from the person 1 who is walking, but the present embodiment explains the physical movement system for calculating the stance (the width between the right foot and the left foot) based on the acceleration data that is obtained in the same manner.

Figure 10:
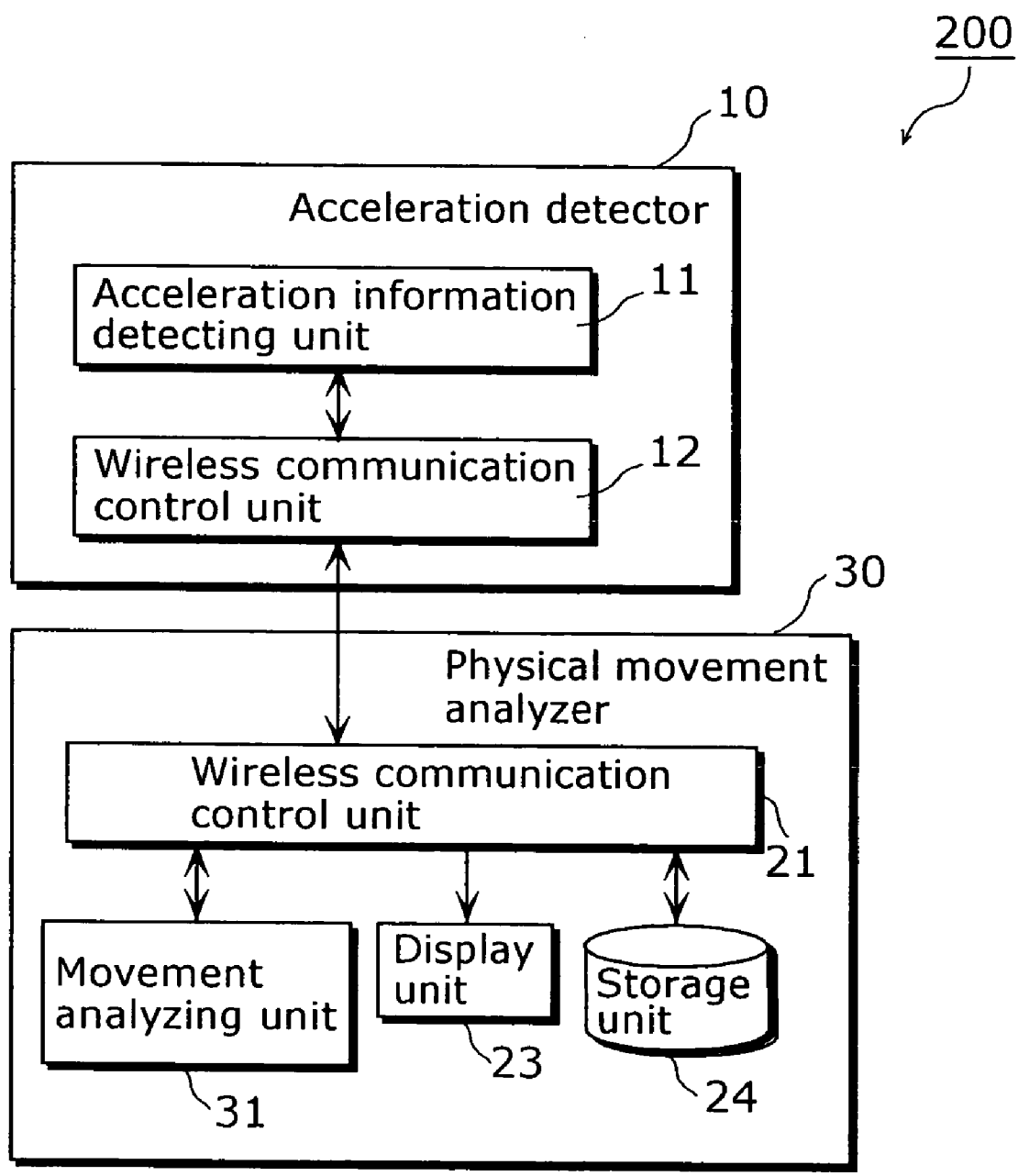
FIG. 10 is a block diagram showing the functional structure of an acceleration detecting apparatus and the functional structure of the physical movement analyzer in the second embodiment.

FIG. 10 is a block diagram showing each functional structure of the acceleration detecting apparatus 10 and the physical movement analyzer 30 in the physical movement analyzing system 200 concerning the present embodiment. The same functional structures as the ones in the physical movement analyzing system 100 in the above-mentioned first embodiment are assigned the same reference numbers and explanations on them will be omitted below.

The acceleration detecting apparatus 10 measures the acceleration of the person 1 at least in a single direction in the back and forth direction, in the right and left direction, and the vertical direction, and outputs the signal that corresponds to the acceleration (called acceleration data below) to the wireless communication control unit 12.

The physical movement analyzer 30 is an apparatus for calculating the stance in walking based on the measured acceleration data, and comprises a wireless communication control unit 21, a movement analyzing unit 31, a display unit 23 and a storage unit 24.

The movement analyzing unit 31 is a unit with a function that corresponds to the walking speed detecting unit 22 in the above-mentioned embodiment 1 and has a function for performing a waveform analysis on the acceleration data that is received from the wireless communication control unit 21 at a predetermined temporal interval.

Figure 11:
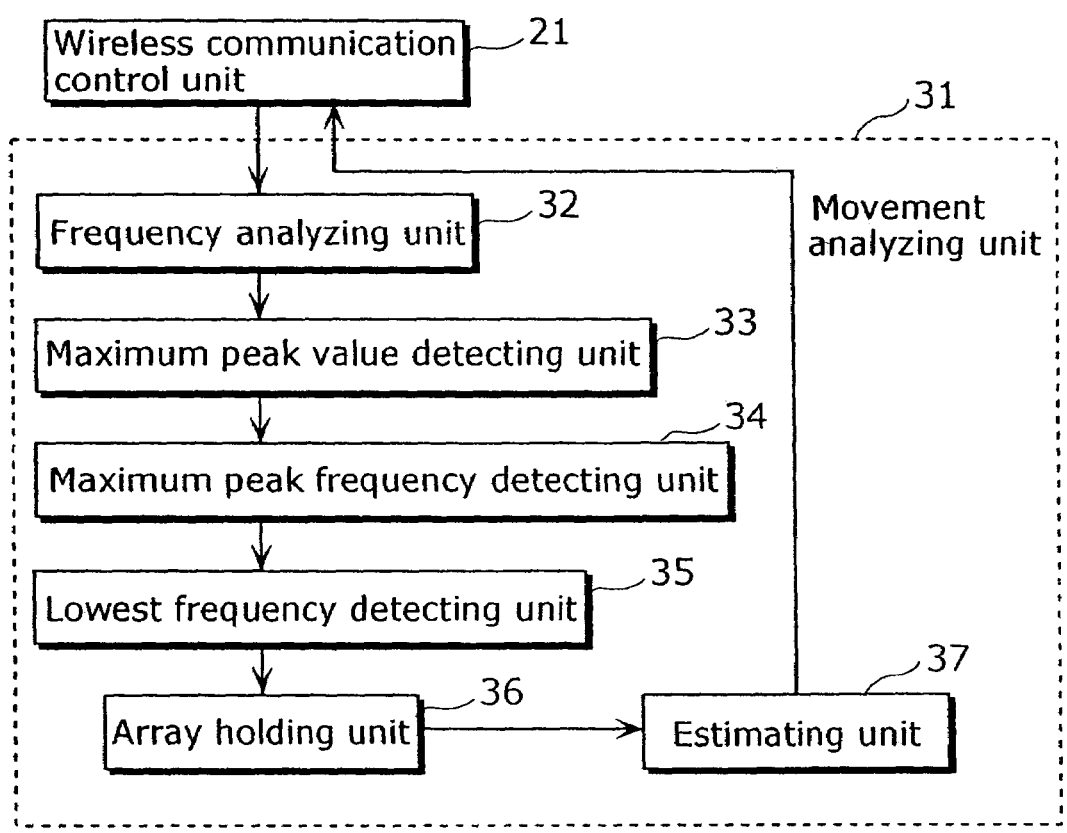
FIG. 11 is a block diagram showing the functional structure of a movement analyzing unit.

FIG. 11 is a block diagram showing the functional structure of the movement analyzing unit 31. As shown in FIG. 11, the movement analyzing unit 31 comprises a frequency analyzing unit 32, a maximum peak value detecting unit 33, a maximum peak frequency detecting unit 34 and a lowest frequency detecting unit 35, an array holding unit 36 and an estimation unit 37.

The frequency analyzing unit 32 executes the frequency analysis on the acceleration data that is received from the wireless communication control unit 21. The maximum peak value detecting unit 33 detects the maximum peak value of the power from the power spectrum that is inputted from the frequency analyzing unit 32. The maximum peak frequency detecting unit 34 detects the frequency corresponding to the maximum value that is detected in the maximum peak value detecting unit 33. The lowest frequency detecting unit 35 detects the lowest frequency except 0Hz in a group of frequencies that are extracted in the maximum peak frequency detecting unit 34. The array holding unit 36 holds the array comprising a lowest frequency, the maximum value corresponding to the lowest frequency and these measurement dates and time. The estimating unit 37 reads out the data of the specified date and time from the data that are stored in the array holding unit 36 and outputs them to the wireless communication control unit 21.

Here, the function of the movement analyzing unit 31 will be explained in detail with reference to the acceleration data in the right and left direction.

Figure 12:
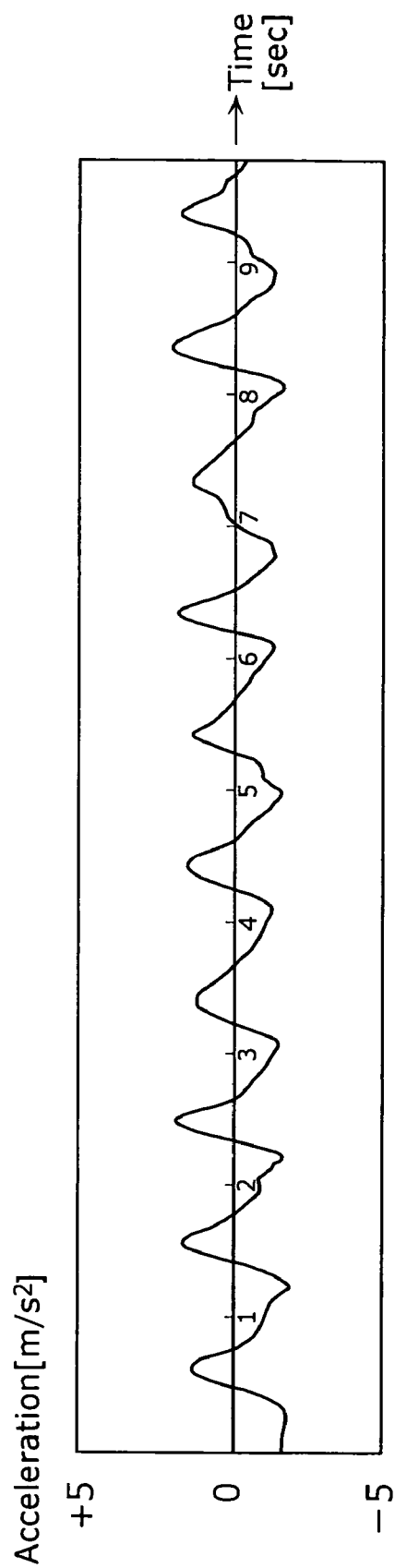
FIG. 12 is an example of time series data of acceleration in the right and left direction in a walking test that is performed on a person.

FIG. 12 is an example of time series data of the acceleration in the right and left direction in the walking test that is performed on the person 1. In the FIG. 12, the horizontal axis shows the time [sec] and the vertical axis shows the acceleration respectively. FIG. 12 is the case of the acceleration data that is collected at a sampling rate of 125 Hz for a 10 second walk.

First, the frequency analyzing unit 32 performs a frequency analysis on the acceleration data that is received via the wireless communication control unit 21, and generates the power spectrum. Next, the maximum peak value detecting unit 33 identifies one or more envelope on the power spectrum that is generated based on the acceleration data and detects the maximum peak value for every identified envelope.

Consequently, the maximum peak frequency detecting unit 34 detects a waveform frequency with the detected maximum peak value.

Figure 13:
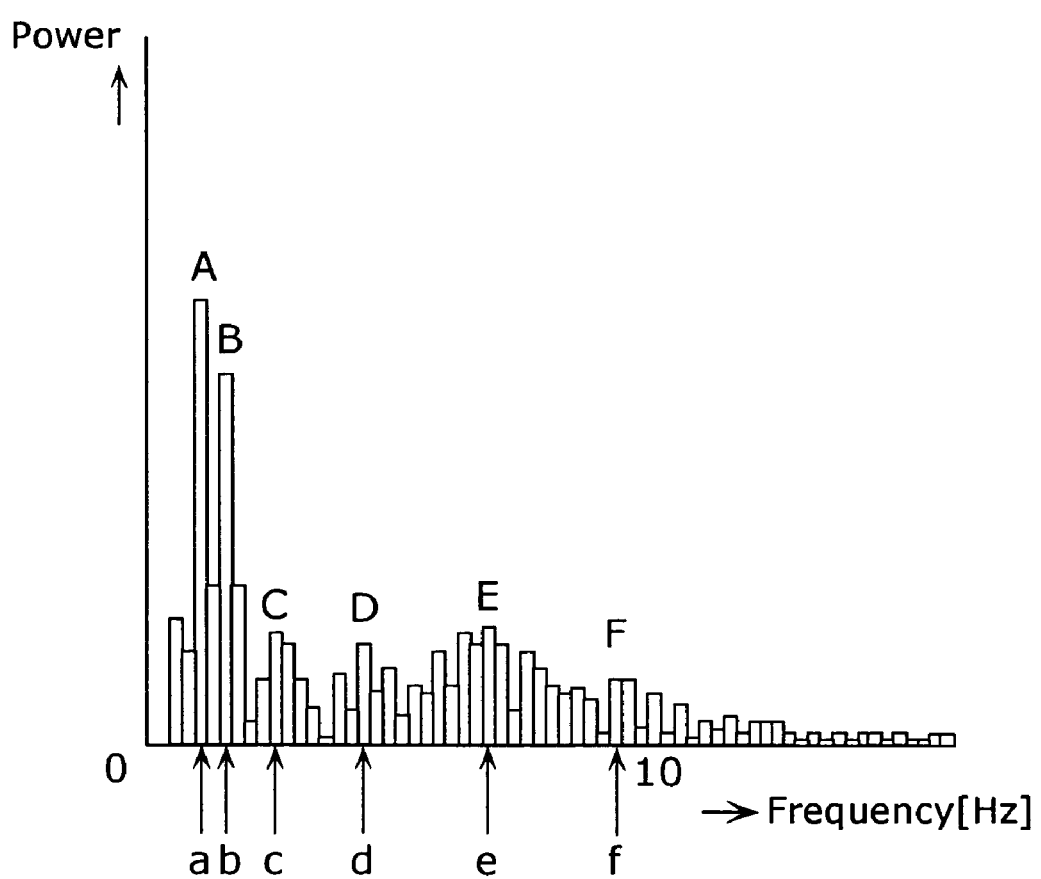
FIG. 13 is a diagram showing an example of a power spectrum that is generated in the frequency analyzing unit.

FIG. 13 is a diagram showing the example of the power spectrum that is generated in the frequency analyzing unit 32. In FIG. 13, the horizontal axis shows frequency [Hz] and the vertical axis shows the power. A to F in FIG. 13 shows the spectrum showing each maximum peak in a plurality of convex parts that are indicated using the envelope that is detected in the maximum peak frequency detecting unit 34, and a to f shows the frequency that corresponds to the respective maximum peak values that are identified by the maximum peak value detecting unit 33.

Next, the lowest frequency detecting unit 35 extracts the lowest frequency except 0Hz in frequencies a to f. In the case of FIG. 13, it corresponds to a. After that, the array holding unit 36 holds the lowest frequency that is identified in the above-mentioned way and this maximum peak value that corresponds to the lowest frequency (it corresponds to A in FIG. 13) associating each of them with each measurement date as an array data.

Consequently, the estimating unit 37 reads out the array data that is stored in the array holding unit 36 according to the indication that is received from the person 1 and his/her caretaker. After that, the data for presenting the maximum peak value to the lowest frequency for every day in graphical form to the wireless communication control unit 21. The wireless communication control unit 21 instructs the display unit 23 to display it based on the data received from the estimating unit 37.

Figure 14:
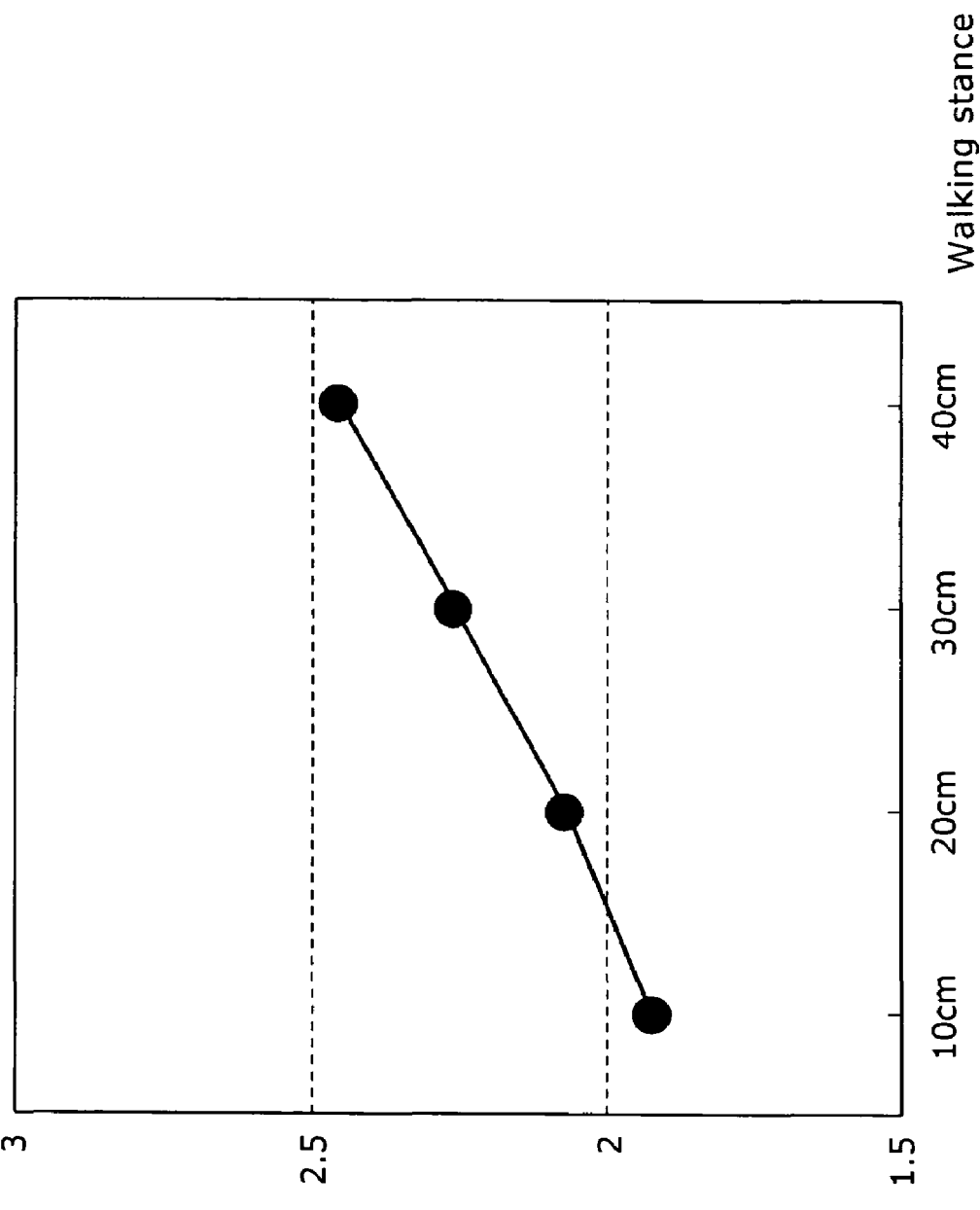
FIG. 14 is a diagram showing an example of the relation between the stance estimating index showing a power value in the lowest frequency and walking stances.

FIG. 14 is a diagram showing the example of the relation between the stance estimation index indicating the power value in the lowest frequency and the walking stance. In FIG. 14, the horizontal axis shows the walking stance [cm] and the vertical axis is the stance estimation index that represents the above-mentioned maximum peak value in a form of the common logarithm. FIG. 14 shows that there is a linear relation between the walking stance and the maximum peak value.

Figure 15:
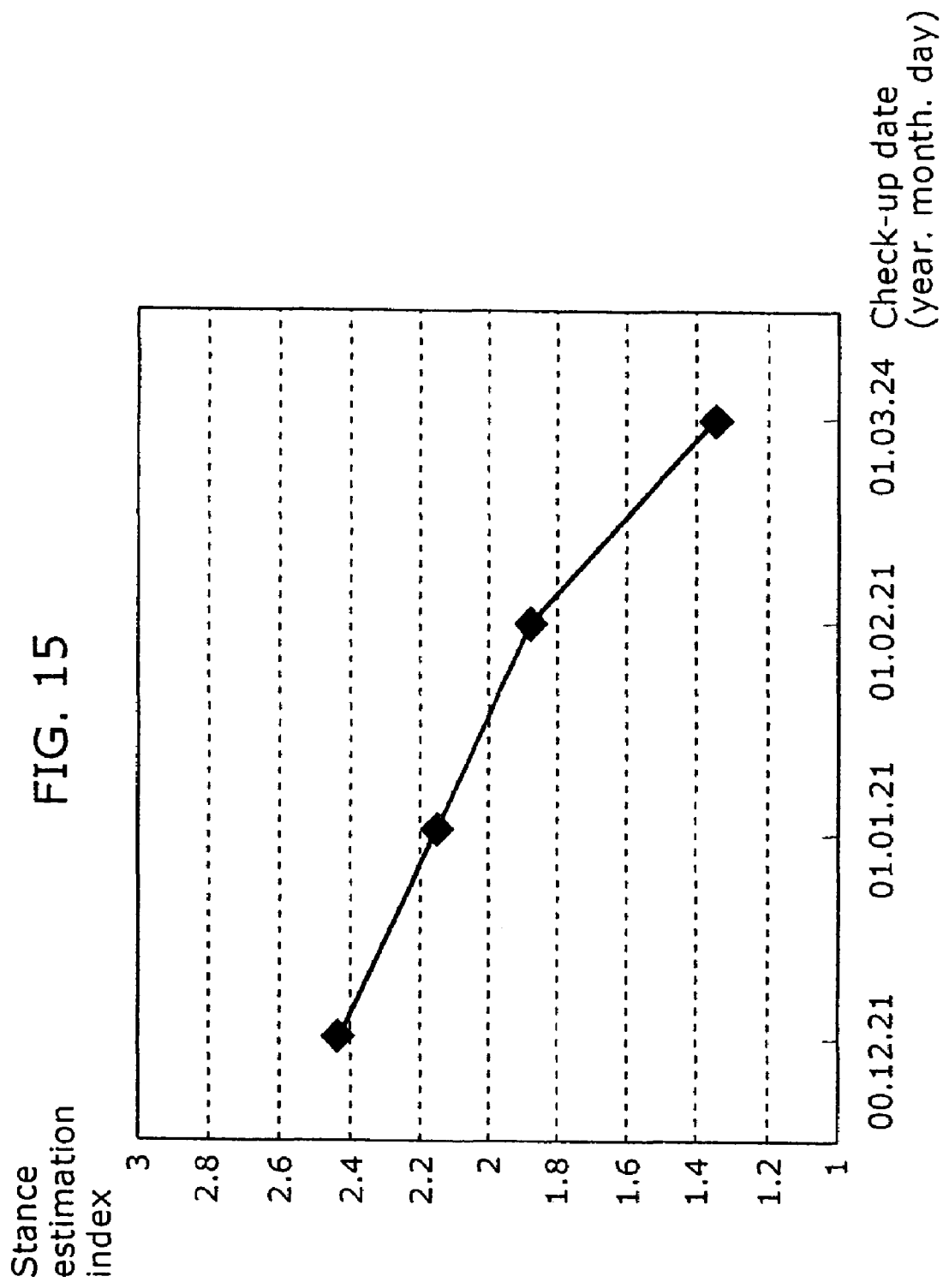
FIG. 15 is an example showing how stances obtained in the walking test change.

FIG. 15 is an example, which is made using the above-mentioned relation in FIG. 14 showing how the stances obtained in the walking test change. In FIG. 15, the horizontal axis shows the date of the walking test and the vertical axis shows the walking stance estimation index.

In FIG. 15, person's walking stance in the right and left direction is getting narrower according to the elapsed time, and it is possible to quantitatively grasp the recovery level of the physical movement ability of a patient with a leg malfunction (person 1).

Figure 16:
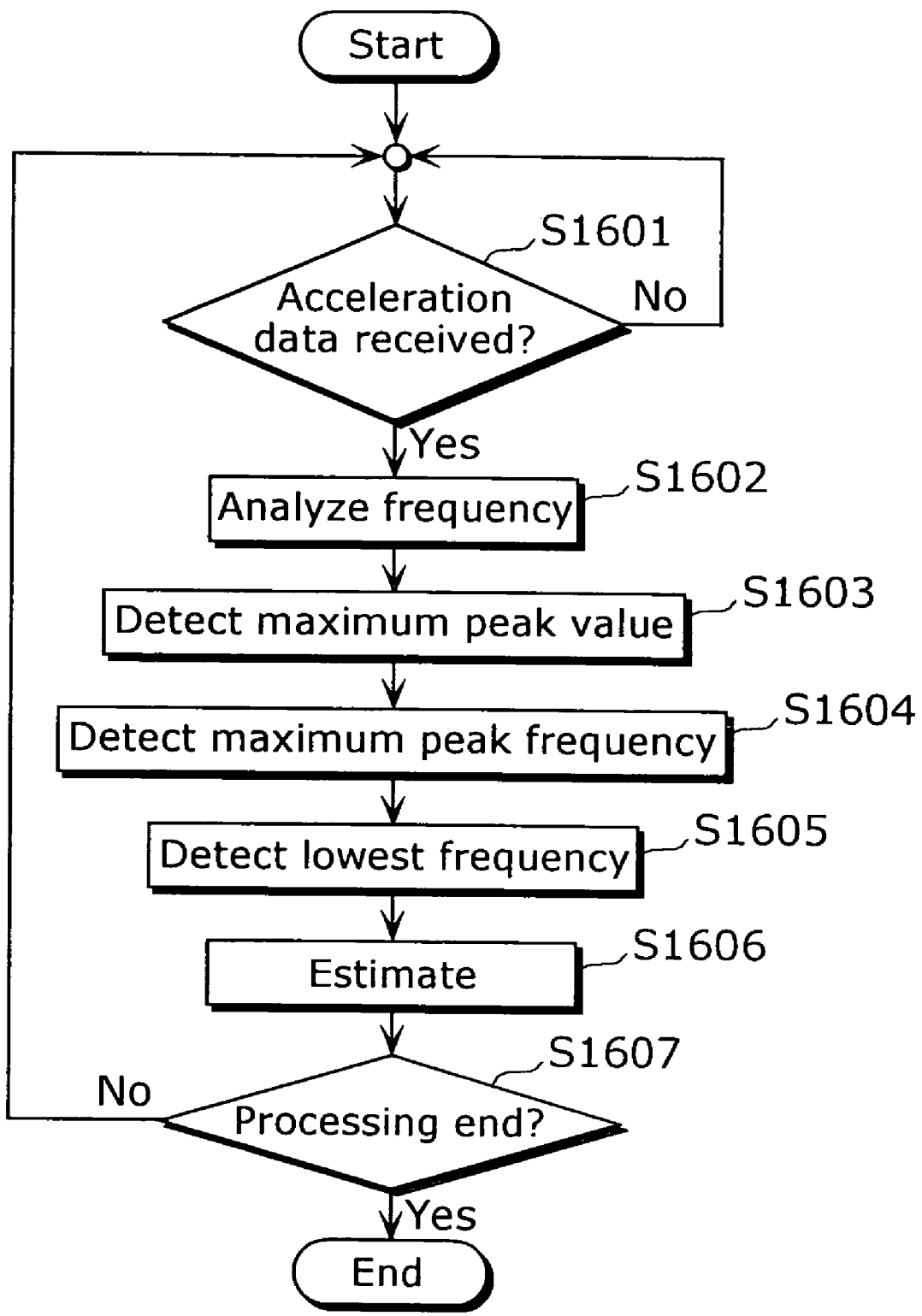
FIG. 16 is a flow chart showing the processing flow of a physical movement analyzing system in the second embodiment.

Next, the operation of the physical movement analyzing system 200 that is formed as shown above will be explained. FIG. 16 is a flow chart showing the processing flow of the physical movement analyzing system 200.

First, the frequency analyzing unit 32 receives the acceleration data from the wireless communication control unit 21 (S1601) and executes a frequency analysis on this acceleration data (S1602) and outputs the result to the maximum peak value detecting unit 33.

Next, the maximum peak value detecting unit 33 detects the maximum peak value of the power from the power spectrum that is inputted from the frequency analyzing unit 32 (S1603). In this way, the maximum peak frequency detecting unit 34 detects the frequency corresponding to the maximum peak value that is detected in the maximum peak value detecting unit 33 (S1604).

Further, the lowest frequency detecting unit 35 detects the lowest frequency except 0Hz in frequencies that are detected in the maximum peak frequency detecting unit 34 (S1605). After that, the array holding unit 36 holds the array comprising the lowest frequency, the maximum peak value corresponding to the lowest frequency and each measurement date.

The estimating unit 37 reads out data of the specified date and time from the data that are stored in the array holding unit 36 and outputs it to the wireless communication control unit 21 (S1606). Next, if the processing is finished (S1607: Yes), then the physical movement analyzer stops analyzing. However, if the processing is not finished (S1607:No), then the wireless communication control unit 21 continues to check for received data (S1601).

As described up to this point, the physical movement analyzing system 200 concerning this embodiment makes it possible to compare the physical movement ability recovery levels of the patient with a leg malfunction day-by-day.

Third Embodiment

The above-mentioned embodiment 1 explains the physical movement analyzing system for calculating the strides, walking speed or the like based on the acceleration data that is obtained from the person 1 who is walking, but this embodiment explains the physical movement analyzing system for quantifying the recovery level of the walking ability based on the difference of the acceleration.

Figure 17:
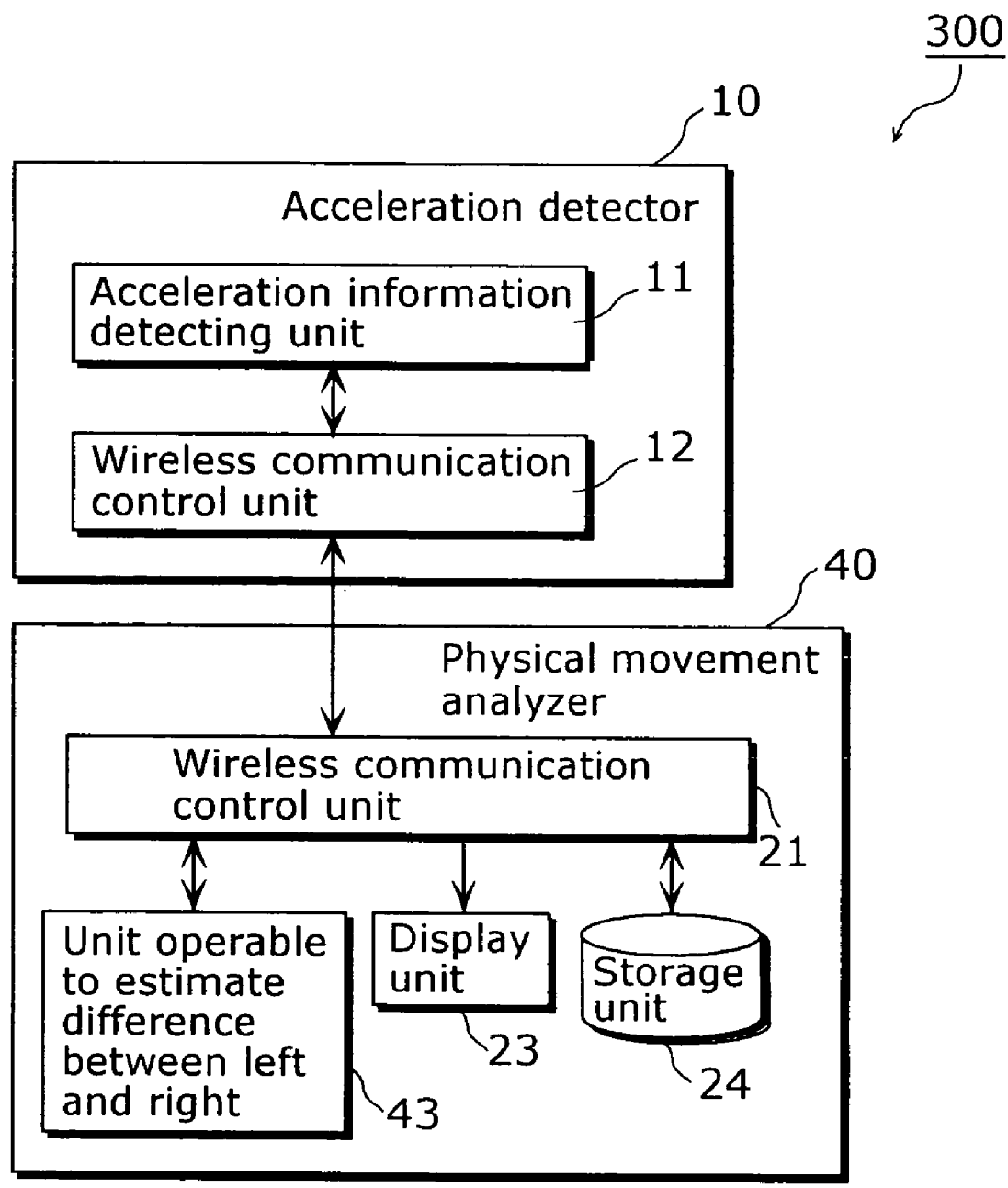
FIG. 17 is a block diagram showing the functional structure of an acceleration detecting apparatus and the functional structure of a physical movement analyzer in the third embodiment.

FIG. 17 is a block diagram showing each functional structure of the acceleration detecting apparatus 10 and the physical movement analyzer 40 in the physical movement analyzing system 300 in this embodiment. This physical movement analyzing system 300 comprises an acceleration detecting apparatus 10 and a physical movement analyzer 40, and it is a system where the acceleration detector 10 measures the acceleration generated by the right foot and the left food separately while the person 1 is walking, and quantifies the walking ability recovery level based on the differences of these measured accelerations. It is provided that walking is an example of person 1's movements below and the acceleration detector 10 measures the acceleration while the person 1 is walking. Also, the same functional structures as the ones in the physical movement analyzing system 100 in the above-mentioned embodiment 1 are given the same reference numbers and explanations on them will be omitted.

The physical movement analyzer 40 equips the function of general personal computers and has the function for receiving the acceleration data that is sent from the acceleration detect a 10 using a communication method or the like based on the above-mentioned Bluetooth and quantifying person's recovery level and the like based on this acceleration data.

As shown in FIG. 17, the physical movement analyzer 40 comprises a wireless communication control unit 21, a unit operable to estimate difference between left and right 43, a display unit 23 and a storage unit 24.

The unit operable to estimate difference between left and right 43 is a processing unit for performing a numerical operation based on the acceleration data that is received from the wireless communication control unit 21 and calculates the estimated points of difference between left and right that indicates the differences of the acceleration in the back and forth direction generated by the right foot and the left foot. To be more specific, the difference between left and right estimating unit 43 judges the foot for acceleration in walking from the acceleration data in the right and left direction and extracts the acceleration data generated by the left foot and the acceleration data generated by the right foot based on the acceleration data in the back and forth direction and calculates the above-mentioned estimated points of difference between left and right as the ratio of these accelerations or the differences of these accelerations.

The display unit 23 is a display apparatus with, for example, a liquid panel and displays the estimated points of difference between left and right that is calculated in the above-mentioned unit operable to estimate difference between left and right 43 in response to the instruction of control made by the wireless communication control unit 21.

The storage unit 24 is a recording medium with, for example, a RAM, a fixed disc or the like, and has an input/output interface for exchanging data between the wireless communication control unit 21. Further, the storage unit 24 records the acceleration data or the estimated points of difference between left and right that are calculated in the unit operable to estimate difference between left and right 43 in a way that they are associated with person 1, measurement date and time or the like in response to the instruction by the wireless communication control unit 21.

Figure 18:
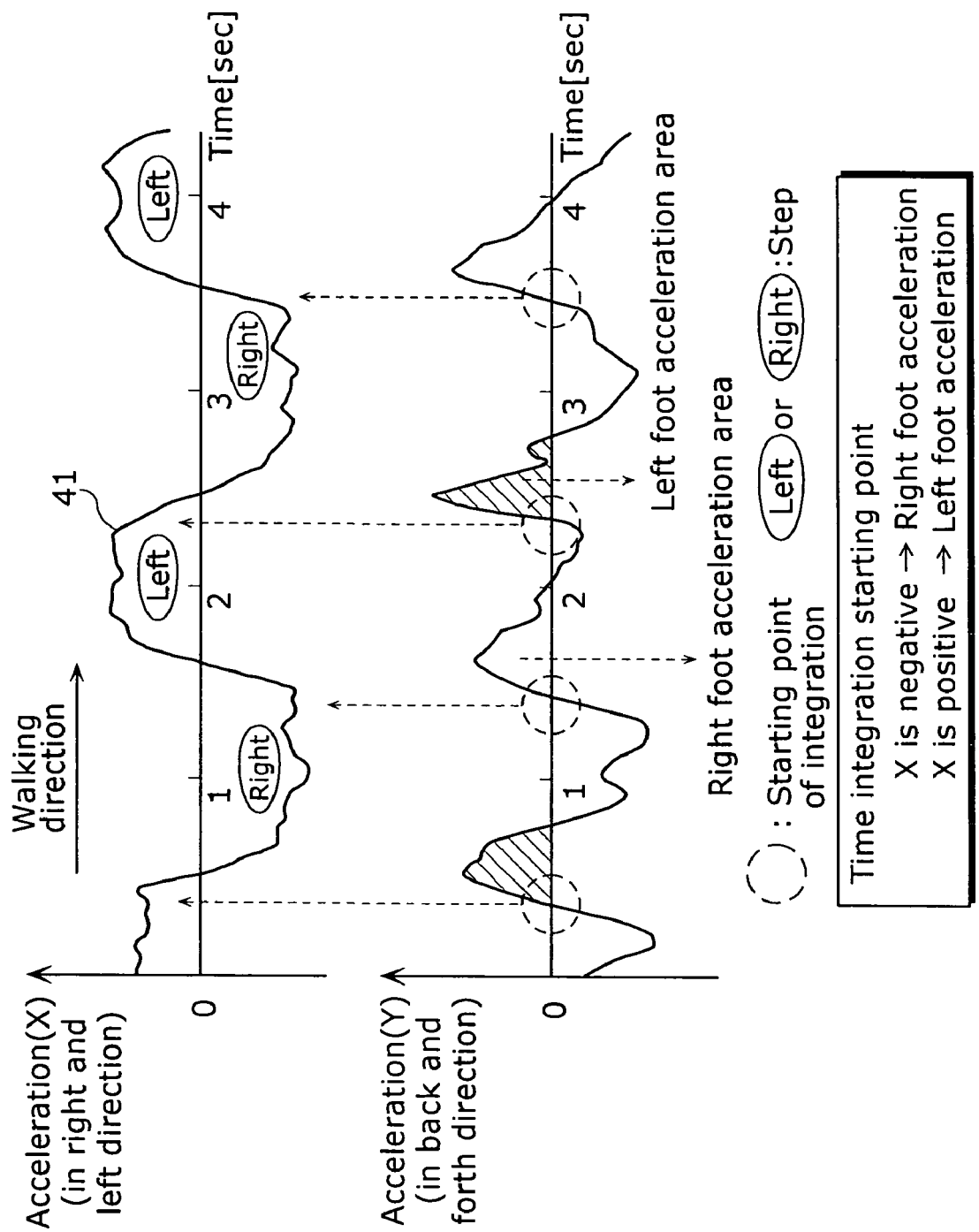
FIG. 18 is a diagram showing the correlation between steps of a person and acceleration data in the right and left direction and in the back and forth direction.

FIG. 18 is an illustration of the processing contents in the above-mentioned unit operable to estimate difference between left and right 43 and a diagram showing the relation between the steps of the person 1 and the acceleration data in the right and left direction or in the vertical direction. As shown in FIG. 18, the upper row in the diagram shows the acceleration in the right and left direction while the person 1 is walking, and the lower row in the diagram shows the acceleration in the back and forth direction. As explained earlier, in this embodiment, "forward" is the positive direction as to the acceleration information in the back and forth information and "rightward" is the positive direction as to the acceleration information in the right and left direction.

The feature of this embodiment is to quantify the person 1's recovery level. Therefore, the difference in speed between the one generated by the right foot and the one generated by the left foot is determined as the estimated points of difference between left and right using a ratio (percentage) of the speed generated by healthy foot to the speed generated by unhealthy foot. That is, it can be obtained from the following formula (3).

[Estimated points of difference between left and right]=[the speed generated by unhealthy foot]/[the speed generated by healthy foot]×100    (3)

As shown in FIG. 18, the speed in the back and forth direction generated by the right foot and the left foot are defined as the value that is obtained by integrating the positive part of the acceleration in the back and forth direction according to the temporal axis, and the other integrating area is defined as the area from the point where the acceleration in the back and forth direction turns to positive to the point where it turns to negative. However, in the case where only the acceleration in the back and forth direction is referred to, it is impossible to judge which foot generates the acceleration, while it is possible to judge the presence/absence of the acceleration. Therefore, this embodiment solves this problem using the acceleration in the right and left acceleration.

In other words, the way steps are generated by the right foot and the left foot makes a difference in the acceleration in the right and left direction. The acceleration in the right and left direction while the left foot is on the ground deviates in the positive direction and the acceleration in the right and left direction while the right foot is on the ground deviates in the negative direction. Referring to the acceleration data in the right and left direction at the time of calculating the speed in the back and forth direction generated by the right foot and the left foot makes it possible to judge which foot generated the acceleration in the back and forth direction.

As shown above, in this embodiment, at the time of calculating the speed generated by the right foot and the left foot, a certain relation that the right foot is on the ground on condition that the acceleration in the right and left direction at the time of starting integration is negative and the left foot is on the ground on condition that the acceleration in the right and left direction at the time of starting integration is positive.

In the integration period, like the case of the above-mentioned embodiment 1, frequency spectrum is generated based on the temporal changes in the measured acceleration and frequency spectrum with a maximum peak value is identified in the generated frequency spectrums. Further, the frequency of the identified frequency spectrum is specified and half of the specified frequency cycle is regarded as the integration period.

Figure 19:
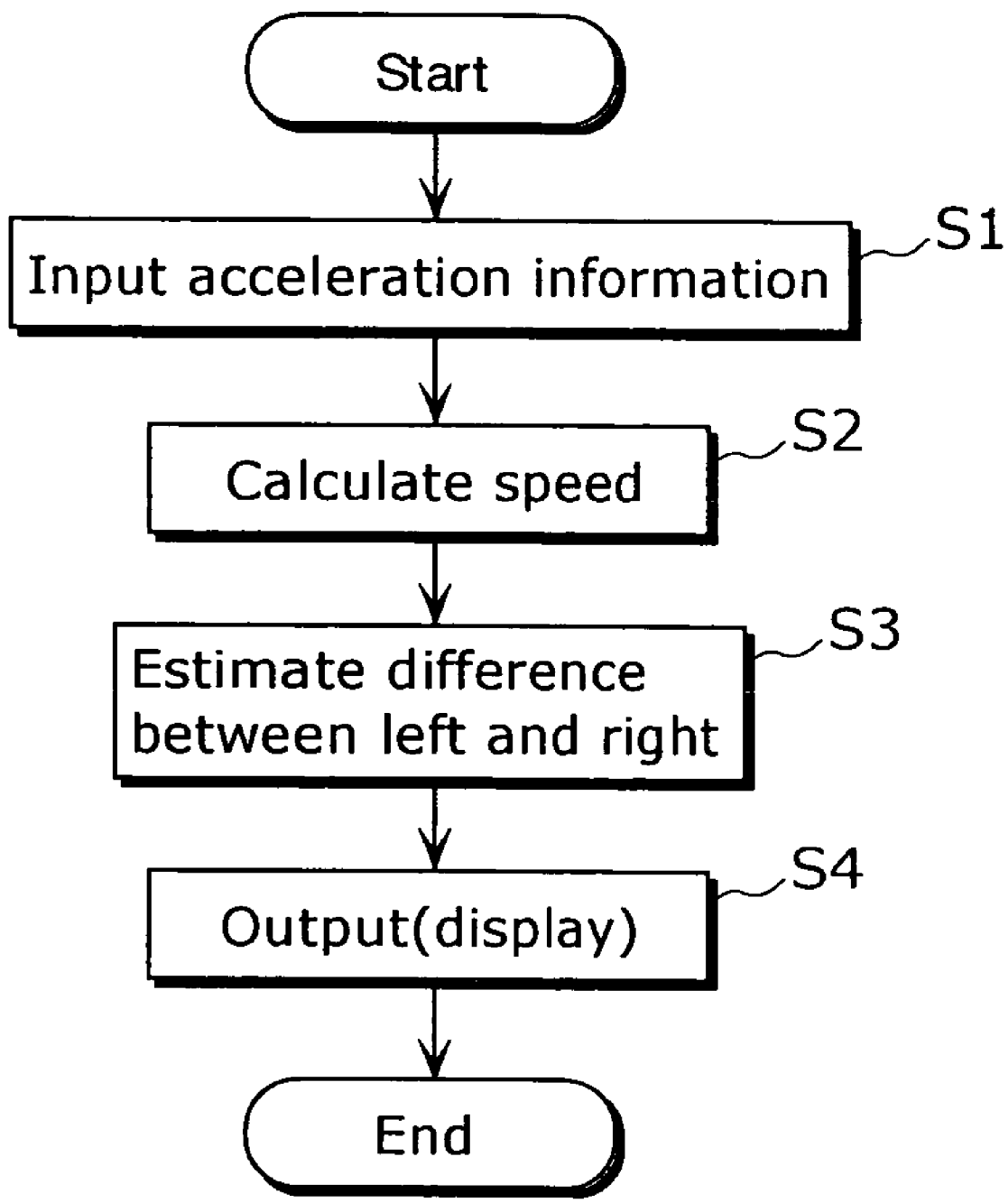
FIG. 19 is a flow chart showing a processing flow of a physical movement analyzing system in the third embodiment.

Next, the operation of the physical movement analyzing system 100 that is formed as shown above will be explained. FIG. 19 is a flow chart showing the processing flow of the physical movement analyzing system 300.

First, when the acceleration data is collected in the acceleration information detecting unit 11 (S1), the unit operable to estimate difference between left and right 43 calculates the speed (S2). Further, the unit operable to estimate difference between left and right 43 calculates the estimated points of difference between left and right (S3) based on the calculated speed, and the display unit 23 displays the calculated estimation points of difference between left and right (S4).

To be more specific, the unit operable to estimate difference between left and right 43 inputs the acceleration information in the back and forth direction and the acceleration information in the right and left direction that are simultaneously measured in a predetermined time area (S1), it calculates the integration value of the inputted acceleration information area-by-area and holds these values.

Further, labels indicating which foot corresponds to each integration value are given to each integration value by referring to the reference numbers of the acceleration in the right and left direction at the time of starting the integration. These integration values that are divided into the ones generated by the right foot and the ones generated by the left foot in this way are averaged and the speed generated by the healthy foot and the speed generated by the unhealthy foot are calculated (S2).

At that time, in the physical movement analyzer concerning this embodiment, information on which foot is the unhealthy foot, that is, that the rest is the healthy foot is previously held, finally, estimated points of difference between left and right that is defined in the above-mentioned formula (3) is generated.

In the case where both feet are healthy, the one that generates a greater acceleration is regarded as the healthy one. This is also true of the case where it is difficult to distinguish the right one from the left one.

Further, the estimated points of difference between left and right that is generated in the step for estimating the difference between left and right (S3) is outputted to the storage unit 23 of the physical movement analyzer concerning this embodiment (S4).

Figure 20:
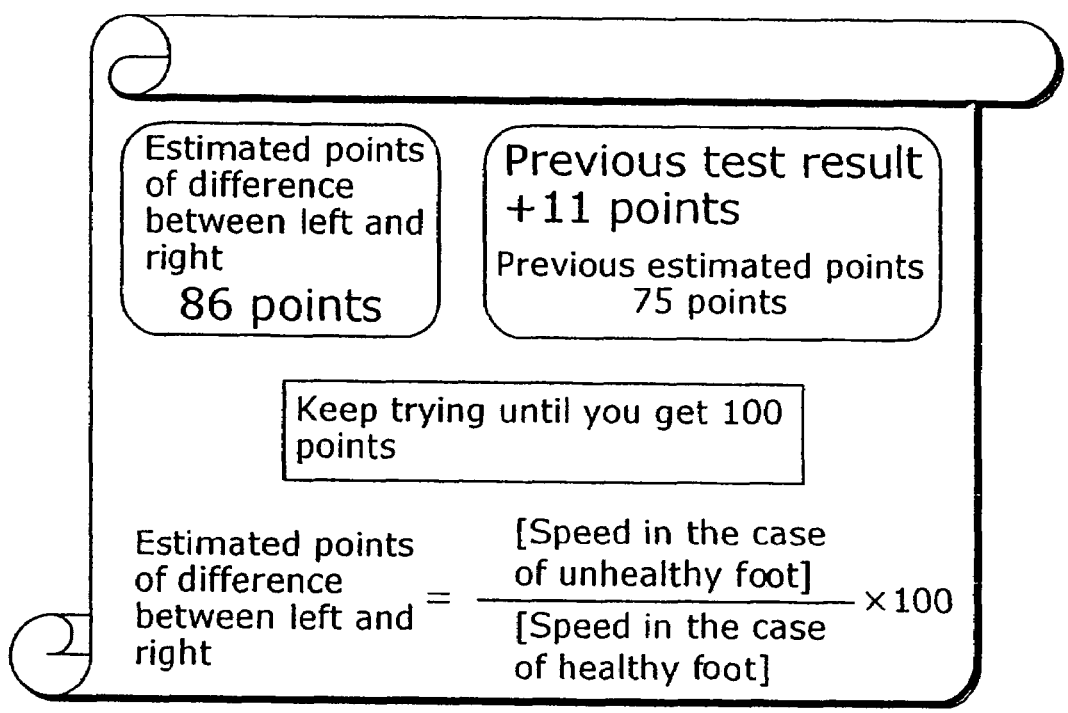
FIG. 20 is a person's display example of estimated points of difference between left and right.

FIG. 20 is an example quantitatively displaying the person's physical movement ability recovery level that is displayed in the display unit 23, and also it is the display example of the estimated points of difference between left and right that is calculated in the above-mentioned formula (3).

In this embodiment, the positive direction in acceleration in the right and left direction is "rightward" and the positive direction in acceleration in the back and forth direction is "forward", but any other case is possible as long as reference numbers can be identified in each direction.

Also, in the above-mentioned embodiment, the display unit 4 is formed in the display apparatus with a liquid crystal panel or the like, but indicators are not limited to the display for a visual representation, any other indicator using, for example, speech synthesis or vibration may be formed so as to perform a representation that appeals to the ear or the touch of sense.

Fourth Embodiment

The above-mentioned third embodiment explains the system for quantifying the walking ability recovery level based on the difference in acceleration of a walking person, but this embodiment will explain the system with a function, which is added to the above-mentioned system, capable of automatically judging the movement of the person is walking or not.

Figure 21:
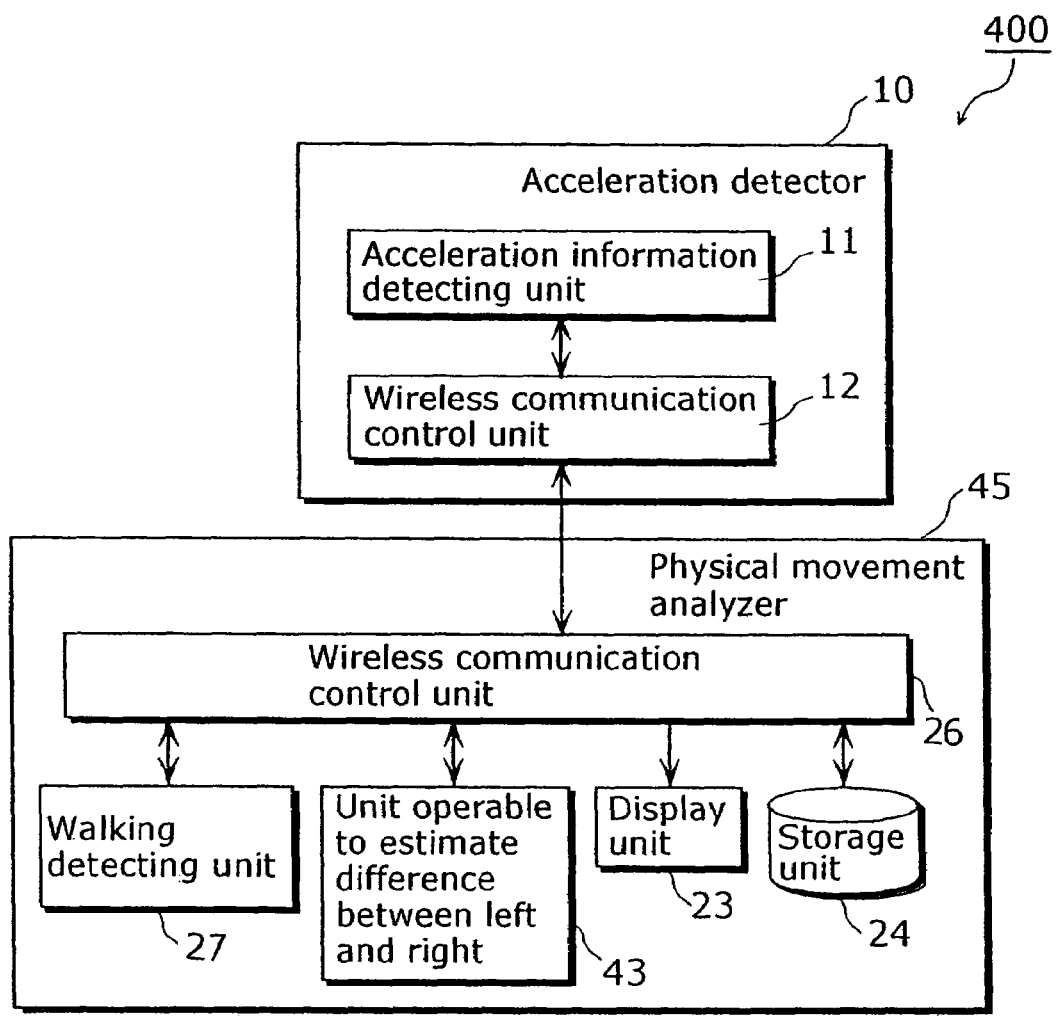
FIG. 21 is a block diagram showing the functional structure of a physical movement analyzing system in the fourth embodiment.

FIG. 21 is a block diagram showing the functional structure of the physical movement analyzing system 400 concerning this embodiment. As shown in FIG. 21, the physical movement analyzing system 400 comprises an acceleration detector apparatus 10 and a physical movement analyzer 45. As to the same functional structure as the ones in the physical movement analyzing system 100 in the above-mentioned first embodiment, the same reference numbers are assigned to them and explanations on them will be omitted.

The physical movement analyzer 45 comprises the function of general personal computers, judges whether the movement of the person is walking or not based on the acceleration data that is sent from the acceleration detector 10, has the function for quantifying the person's recovery level based on the acceleration data in the case where the movement is judged to be walking, and comprises a wireless communication control unit 26, a unit operable to estimate difference between left and right 43, a display unit 23, a storage unit 24 and a walking detection unit 27.

When the wireless communication control unit 26 receives the notification that the movement of the person 1 is walking from the walking detecting unit 27 in addition to the function of the wireless communication control unit 21 in the above-mentioned first embodiment, it instructs the unit operable to estimate difference between left and right 43 to calculate the estimated points of difference between left and right.

The walking detecting unit 27 automatically judges whether the movement is walking or not based on the acceleration data in the inputted vertical direction and notifies the wireless communication control unit 26 of the judgment result.

Figure 22:
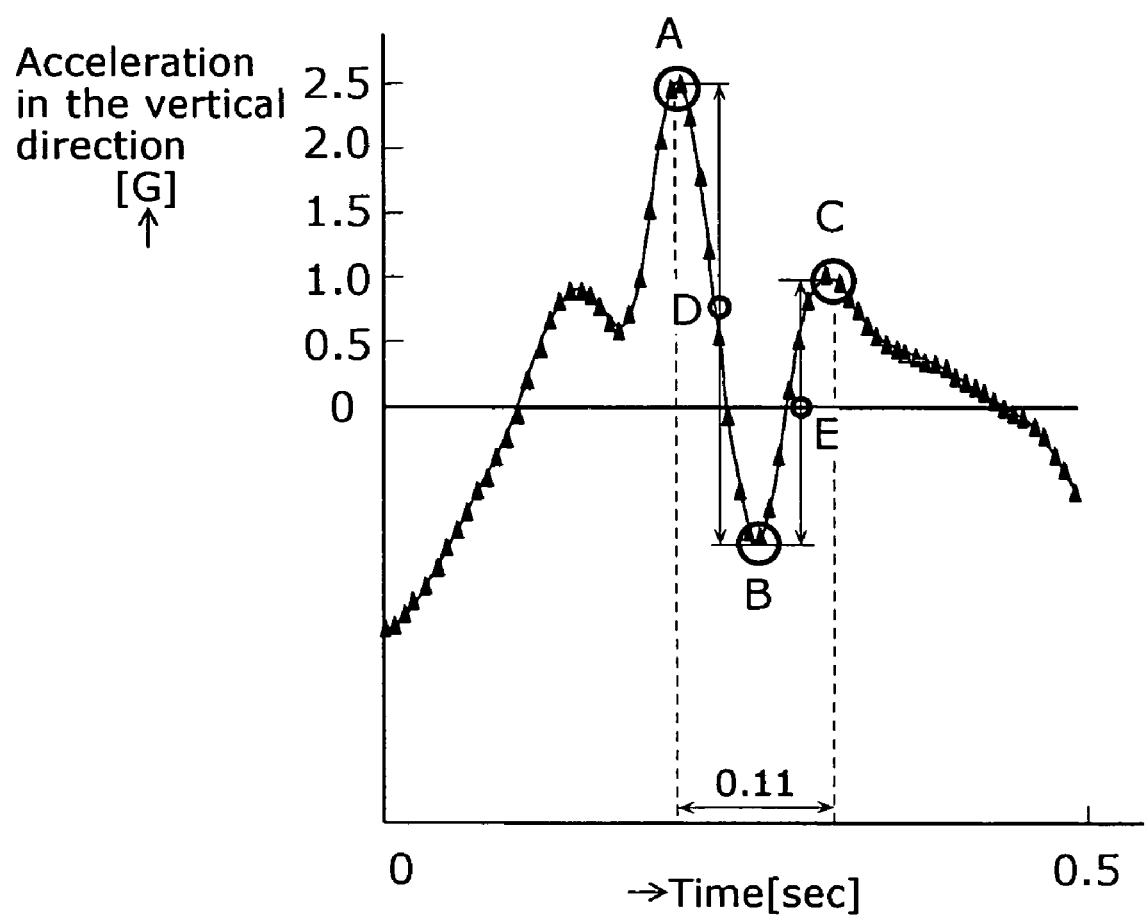
FIG. 22 is a part of a waveform showing the changes, which are referred to at the time of walking estimation in the walking detecting unit, of acceleration in the vertical direction at the time when a person is walking.

FIG. 22 is a part of the waveform, which is referred to at the time of walking judgment in the above-mentioned walking detecting unit 27 indicating changes in acceleration in the vertical direction while the person 1 is walking.

At the time of walking in general, a floor (or a ground) reaction force occurs rhythmically in response that a foot is put on the floor (or the ground). FIG. 22 shows changes of the above-mentioned floor reaction force.

Therefore, the walking detecting unit 27 judges that it is walking in the case where any one of the following two requirements is satisfied:

(requirement 1)

The change "the maximum peak value→the minimum valley value→the maximum peak value" occurs in acceleration in the vertical direction of the predetermined time (for example, 160 [msec]), the amplitude (the amplitude between A and B or B and C in the case of FIG. 22) from the maximum peak value to the minimum valley value (or from the minimum valley value to the maximum peak value) is a predetermined value (for example, 0.15G) or more, and the middle value between the maximum peak value and the minimum valley value (D or E in the case of FIG. 22) is within the predetermined range (for example, from 0.5G to 1.5G).

(requirement 2)

The requirement 1 occurs more than predetermined times (for example, five times) in a predetermined time (for example, two seconds), and the person's posture at that time is standing.

The walking judgment in the above-mentioned walking detecting unit 27 is made during the time period after the acceleration data is obtained and before the acceleration is calculated (that is the time period between the "input of the acceleration information (S1)" and the "calculation of the acceleration" (S2) in FIG. 19 in the above-mentioned third embodiment).

As shown up to this point, the physical movement analyzing system concerning this embodiment makes it possible to collect the three-dimensional acceleration data while the person 1 is walking, judges whether it is walking or not based on these acceleration data, and further, quantifies the walking ability recovery level.

Note that it is also possible to connect the physical movement analyzer 45 in the above-mentioned second embodiment with the terminal (such as a personal computer) in a medical facility that is located in a remote place via a network such as the Internet.

Figure 23:
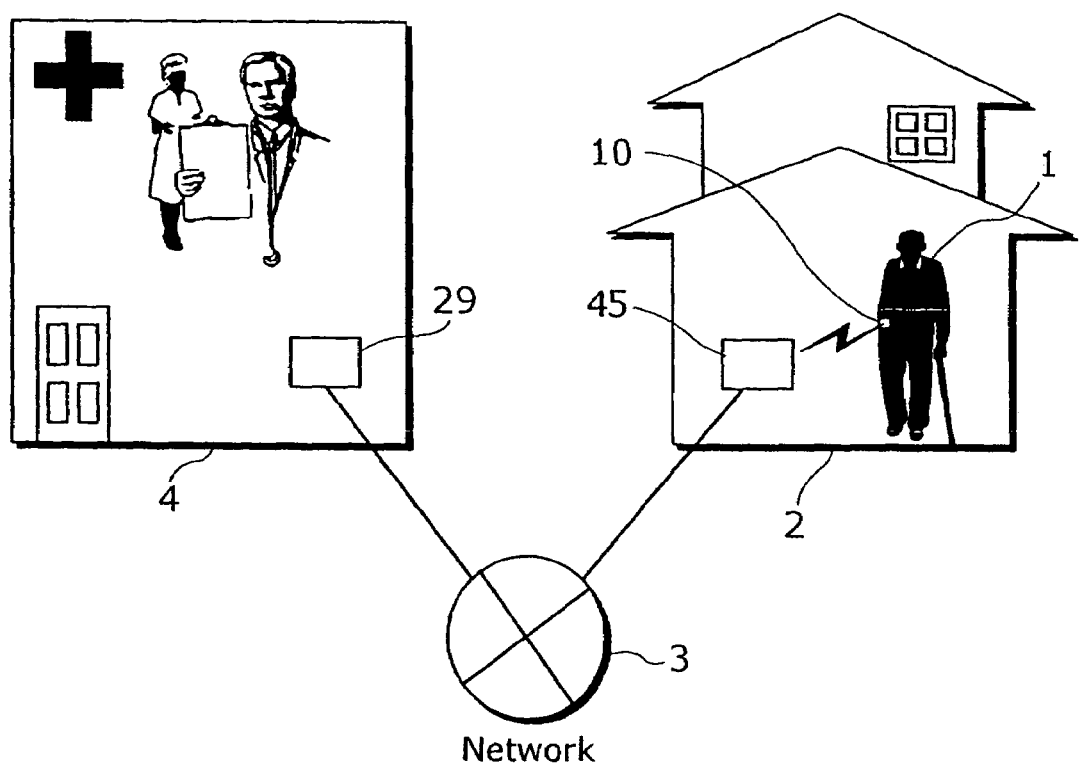
FIG. 23 is a diagram showing how the physical movement analyzer located at person's home is connected with a terminal of a medical facility via a network.

FIG. 23 is a diagram how the physical movement analyzer 45 that is located in the person's home 2 is connected with the terminal 29 in the medical facility 4 via a network 3 as mentioned above.

Connecting the physical movement analyzer 45 with the terminal 29 via the network 3 as shown in FIG. 23 makes it possible to share the information concerning the person 1's recovery or the like with both apparatuses.

FIG. 24 is a diagram showing how person 1's estimated points of difference between left and right that is displayed in the monitor (not shown in any figures) of the above-mentioned terminal 29 changes. In this way, staff members in a medical facility can grasp the person 1's recovery status even in a remote place and also make appropriate advice.

Also, FIG. 24 is an example for displaying the information concerning the physical movement abilities of the person that is displayed on the display unit 23 that is installed in the terminal 29 in the medical facility 4 via a communication line, and the function of the display unit 23 presents the past estimated points of difference between left and right that changes as the number of postoperative days increases in graphical form.

Quantitatively indicating the physical movement ability recovery of the person to the medical staff in this way makes it possible to facilitate the progress management of the functional recovery. Also, utilizing the communication line makes it possible to share the functional recovery level among staff members and the patient at home.

As described up to this point, the physical movement analyzing system 400 in this embodiment can detect walking automatically and facilitate the autonomic rehabilitation by representing the physical movement ability to the person.

Note that the embodiment for fixing the acceleration detector 10 on the right waist of the person 1 has been explained in the above-mentioned embodiment 1 to 4. It is preferred that the apparatus be put on the trunk, not on the other parts such as an arm and a leg in the case of calculating the change of the walking stance in the right and left direction. Further, the nearer to the center of the trunk the right waist is, the better.

Also, the above-mentioned first to fourth embodiments indicates an example for collecting acceleration data at a sampling rate of 125 Hz, but the sampling rate may be the one that is capable of obtaining acceleration waveform that is included in the frequency band ranging from at least 0 to 20 Hz.

Further, embodiments 1 to 4 show an example for performing physical movement analysis on walking, but it is possible to apply it to a judgment whether or not it is beautiful walking based on the person's height, weight or the like. Also, it can be applied to the analysis on running form in jogging or marathon and used for study of an efficient good running form.

Note that the above-mentioned fourth embodiment determines the predetermined time in the requirement 2 is "two seconds", but this value may be set at an arbitrary value according to the status of the person 1 or the like.

INDUSTRIAL APPLICABILITY

As described up to this point, the physical movement analyzing system and the physical movement analyzer of this invention may be applied as a rehabilitation system, a sport training apparatus, a terminal device in a rehabilitation facility, a communication terminal in a home of elderly people.

What is claimed is:

1. A physical movement analyzer for analyzing a person's walking ability, the physical movement analyzer comprising:
   an acceleration detecting unit operable to detect an acceleration in a back and forth direction of a person's movement, the acceleration being detected for a period of time; and
   an acceleration analyzing unit operable to calculate a walking stride based on the detected acceleration, the acceleration analyzing unit comprising:
   a spectrum generating unit operable to generate a frequency spectrum based on a curve representing the detected acceleration;
   a maximum spectrum identifying unit operable to identify a maximum spectrum component of the generated frequency spectrum;
   a logarithm value calculating unit operable to calculate a common logarithm value based on a peak value of the identified maximum spectrum component; and
   a walking stride calculating unit operable to calculate the walking stride by applying the calculated common logarithm value to a previously defined expression.

2. The physical movement analyzer according to claim 1, wherein the acceleration analyzing unit is operable to calculate a walking period based on the detected acceleration, the physical movement analyzer further comprising:
a walking ability value calculating unit operable to calculate a walking speed based on the calculated walking stride and the calculated walking period.

3. The physical movement analyzer according to claim 2, wherein:
the acceleration analyzing unit is operable to detect an acceleration in a right and left direction of the person's movement, the acceleration in the right and left direction being detected for the period of time; and
the acceleration analyzing unit comprises:
a zero cross-point identifying unit operable to identify zero cross-points in a curve representing the acceleration detected in the right and left direction; and
a walking period calculating unit operable to calculate the walking period based on at least two identified zero cross-points.

4. The physical movement analyzer according to claim 1, wherein the acceleration analyzing unit is operable to detect an acceleration in a right and left direction of the person's movement, the acceleration in the right and left direction being detected for a period of time, and calculate a walking period based on the acceleration detected in the right and left direction, the physical movement analyzer further comprising:
a walking ability value calculating unit operable to calculate a walking speed based on the calculated walking stride and the calculated walking period.

5. The physical movement analyzer according to claim 4, wherein the acceleration analyzing unit comprises:
a zero cross-point identifying unit operable to identify zero cross-points in a curve representing the acceleration detected in the right and left direction; and
a walking period calculating unit operable to calculate the walking period based on at least two identified zero cross-points.

6. A physical movement analyzing system comprising:
an acceleration detecting apparatus comprising:
an acceleration detecting unit operable to detect an acceleration in a back and forth direction of a person's movement, the acceleration being detected for a period of time, and
an acceleration sending unit operable to transform the detected acceleration into an electric signal and send the electric signal to the analyzer; and
an analyzer for analyzing a person's walking ability, the analyzer comprising:
an acceleration receiving unit operable to receive the electric signal sent from the acceleration detecting apparatus, and operable to transform the received electric signal into the detected acceleration, and
an acceleration analyzing unit, operable to calculate a walking stride based on the detected acceleration, comprising:
a spectrum generating unit operable to generate a frequency spectrum based on a curve representing the detected acceleration;
a maximum spectrum identifying unit operable to identify a maximum spectrum component of the generated frequency spectrum;
a logarithm value calculating unit operable to calculate a common logarithm value based on a peak value of the identified maximum spectrum component; and
a walking stride calculating unit operable to calculate the walking stride by applying the calculated common logarithm value to a previously defined expression.

7. The physical movement analyzing system according to claim 6, wherein:
the acceleration analyzing unit is operable to calculate a walking period based on the detected acceleration; and
the analyzer further comprises a walking ability value calculating unit operable to calculate a walking speed based on the calculated walking stride and the calculated walking period.

8. The physical movement analyzer according to claim 6, wherein:
the acceleration analyzing unit is operable to detect an acceleration in a right and left direction of the person's movement, the acceleration in the right and left direction being detected for the period of time;
the acceleration analyzing unit is operable to calculate a walking period based on the detected acceleration in the right and left direction; and
the analyzer further comprises a walking ability value calculating unit operable to calculate a walking speed based on the calculated walking stride and the calculated walking period.

9. A physical movement analyzing method for analyzing a person's walking ability, the physical movement analyzing method comprising:
detecting, for a period of time, an acceleration in a back and forth direction of a person's movement; and
analyzing the detected acceleration to calculate a walking stride by:
generating a frequency spectrum based on a curve representing the detected acceleration;
identifying a maximum spectrum component of the generated frequency spectrum;
calculating a common logarithm value based on a peak value of the identified maximum spectrum component; and
calculating the walking stride by applying the calculated common logarithm value to a previously defined expression.

10. The physical movement analyzing method according to claim 9, wherein the analyzing of the detected acceleration further includes calculating a walking period based on the detected acceleration, the physical movement analyzing method further comprising:
calculating a walking speed based on the calculated walking stride and the calculated walking period.

11. The physical movement analyzing method according to claim 9, wherein the detecting of the acceleration further includes detecting, for the period of time, an acceleration in a right and left direction of the person's movement, and the analyzing of the detected acceleration further includes calculating a walking period based on the acceleration detected in the right and left direction, the physical movement analyzing method further comprising:
calculating a walking speed based on the calculated walking stride and the calculated walking period.

12. A computer program recorded on a computer-readable recording medium, the computer program for analyzing a person's walking ability, and the computer program causing a computer to execute a method comprising:
detecting, for a period of time, an acceleration in a back and forth direction of a person's movement; and
analyzing the detected acceleration to calculate a walking stride by:

generating a frequency spectrum based on a curve representing the detected acceleration;

identifying a maximum spectrum component of the generated frequency spectrum;

calculating a common logarithm value based on a peak value of the identified maximum spectrum component; and calculating the walking stride by applying the calculated common logarithm value to a previously defined expression.

13. The computer program according to claim 12, wherein:

the analyzing of the detected acceleration further includes calculating a walking period based on the detected acceleration; and the physical movement analyzing method further includes calculating a walking speed based on the calculated walking stride and the calculated walking period.

14. The computer program according to claim 12, wherein:

the detecting of the acceleration further includes detecting, for the period of time, an acceleration in a right and left direction of the person's movement;

the analyzing of the detected acceleration further includes calculating a walking period based on the acceleration detected in the right and left direction; and the physical movement analyzing method further includes calculating a walking speed based on the calculated walking stride and the calculated walking period.

* * * * *